(12) United States Patent
Bailey et al.

(10) Patent No.: US 8,101,354 B2
(45) Date of Patent: Jan. 24, 2012

(54) METHOD FOR SCREENING FOR A TOBIANO COAT COLOR GENOTYPE

(75) Inventors: Ernest Bailey, Lexington, KY (US);
Samantha A. Brooks, Newfield, NY (US)

(73) Assignee: University of Kentucky Research Foundation, Lexington, KY (US)

( * ) Notice: Subject to any disclaimer, the term of this patent is extended or adjusted under 35 U.S.C. 154(b) by 245 days.

(21) Appl. No.: 12/353,524

(22) Filed: Jan. 14, 2009

(65) Prior Publication Data

US 2010/0184025 A1 Jul. 22, 2010

Related U.S. Application Data

(60) Provisional application No. 61/021,129, filed on Jan. 15, 2008.

(51) Int. Cl.
*C07H 21/04* (2006.01)
*C12Q 1/68* (2006.01)

(52) U.S. Cl. ...... 435/6.1; 435/6.11; 435/6.12; 435/69.1; 536/23.1; 536/24.3

(58) Field of Classification Search .......... None
See application file for complete search history.

(56) References Cited

U.S. PATENT DOCUMENTS

| | | | |
|---|---|---|---|
| 4,898,814 A | 2/1990 | Kwon | |
| 5,413,923 A | 5/1995 | Kucherlapati et al. | |
| 5,416,260 A | 5/1995 | Koller et al. | |
| 5,532,158 A | 7/1996 | Suzuki et al. | |
| 5,545,806 A | 8/1996 | Lonberg et al. | |
| 5,574,205 A | 11/1996 | Kucherlapati et al. | |
| 5,583,278 A | 12/1996 | Alt et al. | |
| 5,625,121 A | 4/1997 | Klein et al. | |
| 5,679,511 A | 10/1997 | Kwon | |
| 6,183,955 B1 | 2/2001 | Anderson et al. | |
| 6,372,900 B1 | 4/2002 | Metallinos et al. | |
| 6,514,747 B2 | 2/2003 | Woychik et al. | |
| 2005/0191242 A1 | 9/2005 | Brissette et al. | |

OTHER PUBLICATIONS

Haase et al. (Animal Genetics, vol. 39, pp. 306-309, E-pub: Apr. 10, 2008).*
Brooks et al. (Cytogenet Genome Res. vol. 119, pp. 225-230, E-pub: Feb. 1, 2008).*
Lindblad-Toh, K. et al.; "The Genome Sequence of *Equus caballus* (horse)"; Gen Bank Accession No. AAWR00000000.1 (Jan. 18, 2007).
Linblad-Toh, K. et al.; "The Genome Sequence of *Equus caballus* (horse), Assembly Version 2.0"; Gen Bank Accession No. AAWR00000000.2 (Sep. 6, 2007).
Brooks, S.A. et al.; "*Equus caballus* chromosome 3 inversion breakpoint, genomic sequence"; Gen Bank Accession No. EF442014.1 (Feb. 15, 2007).
Bowling, Ann Trommershausen;The Journal of Heredity 78:248-250,1987; "Equine linkage group II: phase conservation of To with AIB and GcS"; © 1987, American Genetic Association.
Raudsepp,Terje; Mammalian Genome 10,77-282 (1999); Comparison of horse Chromosome 3 with donkey and human chromosomes by cross-species painting and heterologous FISH mapping.
S.A. Brooks, R.B. Terry and E. Bailey A PCR-RFLP for KIT associated with tobiano spotting pattern in horses Animal Genetics, 33, 301-303 © 2002 International Society for Animal Genetics.

* cited by examiner

*Primary Examiner* — Jeanine A Goldberg
(74) *Attorney, Agent, or Firm* — King & Schickli, PLLC

(57) ABSTRACT

A method for screening for a Tobiano genotype includes obtaining a nucleic acid from an equine animal, and analyzing the nucleic acid for the presence of an inversion in a chromosome ECA3q which is indicative of the genotype for Tobiano. The method includes detecting at least one of a telomeric breakpoint of an inverted ECA3q chromosome and/or a centromeric breakpoint of an inverted ECA3q chromosome. In one embodiment, the nucleic acid may be analyzed by the steps of hybridizing the group of probes or primers having the sequences set forth herein in SEQ ID NO:8, SEQ ID NO: 9, and SEQ ID NO: 10, or sequences complementary thereto, and preparing an amplification product. A 209 bp nucleic acid amplification product (SEQ ID NO:11) indicates the presence of the inversion.

13 Claims, 8 Drawing Sheets

```
TATATTTAAATACTCAGAGCAATTATGAAACCCCACACAGCCTCAACAGACCATTTAACC
TTGAGCAGTGTAATTTCCGGGTGTGTCCTGAAAATAAGTTGGCAACTAATCATATATAGA
AGTAAATAAATGAGTCAAAATATGTCTAAAATGAAGTTATAAGTCAAGTAAGTATTGTTT
TGTATCTAAAGGAATAATGGGTTTGTTTTTAGTGGAATTGATCACTTCTTTTTTGGCAGT
AATTAAGTAGTAGACCAACTTGGAATTTTAGAATCATAAAAGTGAAATTCATTTTTAATA
AATTTTTTTAAATAAAATTCTTAGAAAATGGAATTCAATCTACGCTGTGGGATTTTGTTT
CTTTGGCGTGGCAATGGAGCTGACATTGCAGAATGAGATGTGGCGAAGAATGGCTGCTCT
CCAACACTGTATACAGGTTTTCTTAAATTAACGGCTAGATTGTAAACTTCACCAAAGCAG
AGAACACCTTCTTTTTGACTGTTTTATCCCTGGCCCTCAGCAGAGCGCTGGCATATAGGA
GATCATAGCTGAAATAGCTGCTGTTTTTACCTTGAACACTGTTCTCTGGTACAACAAAAA
TGATAAAAGTCATCAAGAGAGGTTAGAGTTTTTACGTAAATGTTATGCATTTAAAAGTAT
AAGATATATGTTTGTATTAAAATAGTATCTACTTTTAATCAGTGACATGTGATTCCTTCT
TTAATTGAAAAGAAAGCTGTCACATTTTAATCAATGGTCTATGACAGTGTAGGAGGCGTG
ATAGCCAATAAAACATTTTTACATGGCACTTTTCCTCACTCCTTTGAAATCGGAAGCCTC
TAAATAGATATTCTGAACAAAATATATAGCCCAAGTACGATCCAACTTAGAAATGGAAAA
AATACAGAAAAGTTTATTGTAACATATTGGAAATCTTAATATGATGAAACAAAATGAGCT
GCCCAAATTTTGGGGACGATGGTTCTGCATTTGCAGGTCATTTTGGTAATTAAAATATGG
TAAATACCAGCTGTTTCTTATGCTCTTAGATTATCTGTTCATGTTACCAGGATGATTTTG
TGAAGCCGAGTATCAGACTCCATGTCTTAGCAGGCTCAAAGGTCAAAATTAGAATCTTAA
ATTGAAGTTCGCATTAATCCAGATTGCCATTTGCTTACTTTTTGATAGCAGTCCACCTAA
ACTGAAATGAGTAATAGAGATTTTCATGTCTGAATGATATTCCTGCCAGCACCACCAACT
GTTGAATGTTAAGTATGAGATTTGGCAGGTGCAGAGATTTTTAGTCACCTTCAAAAAGCA
ATATGCAGACACCCAAGCCAAACAGCTTATATATTAACAAAATCAACATCCAAACCATCT
GCCAATGGAACAAACATGTCAGTCATCTTTCCATTTGATTGGCAGGGTTTCTAGAAATGA
ATGATTTTAAACATTATTTCTCATCCCAAAAAAAACACACAGGGAATTTTATTTACCTGGT
AATTGAGCTGACTCTGGGCAAAATTATGTAGTTAAAAACGTCTTCATCTTCTCCTTGCTC
TTTCATTGCCTGCTCCTCCGTTACCACTGTGTACCCTGCACACCCATCCTAGCACCTGTT
ATTAACTTATTGACTCCTGCCTGCTGCTGTGCCAAACAGCGCCAGGATGAGTTAATGCTT
GCATCTGATTTATTTCCTCTTAGCCAACATACGTTTTTTAGGACTCTGCTTATAGGCGAT
TATATTTAGTAATTAAATCAGGTAAACCAATTCTTTTAAATTAAATTCTTAAGTTAAAAA
TGACTGACATATAAAACATGATTTTTCACCCTCTAAAAGTCTTTAAAGCGTAAGCATAAA
TCTTTTAAACGCTTGTTTCTCTAGTCGGCTTGGGAAATTGTCAGCCTATTCAGTGCCA
CTGAAATTAGAGGTTTTAAGCAGCCGTGTAATGTCTGCTCATCTATCTGGCTAACCCTGT
TTGGAAAATTCTGCTGACAAATGACTCTGGTATGATTTGGCAGTGGTAGCAGAAGGTCAG
AATCTCTGAGGTTTGGCAGACTGTCTGAAGTTTCAGAGGACCTAATTCCTCACTAAACAG
ACGGATTCTTCTTCATTCAATGAAGTGCTAGACTGACTTTAACAATAACAACAAAAATTC
AGCTGCTAGTCTGTGTGTTTAAATTAGGGGCTACTTGAATCAGAGAGAAAAAAATAGATG
TGGATTTGTATCATTTTATATTTTATTTTCTACTTTCATGTAAGCTGATACAATTTATTT
TTACTTTTAAAAGGAGAGGAATTAGGTACAGAGAATTCTGTAACATTTATCCTGTCTTTC  ← ECAtoR
ACCACAGAGTATCCAATTATGTCTTTCACATAATGCAAAATCTTCAGCACATAGAACACA
TTTTAAATTTACGGCTCAGAGGGATTTCAATCATCTTTGGCATTCAGCACTCAAGGCATT
TCAGATATTTATTCAGAGCAGTATAACAGAAAGTACAC|AGCAGATTGTAATTTAAATGCT
GTACTTTTTGCAACATATATTTGCAATAAAAGCATAGAGAATATGTAAAAATAAGAATGT  ← ECA3Fc
ATTATGAGTACTGCACATTTTCACTACACCCTTTGATAAGGGAATTCTTGCATACTTTCA
TGTAATAGACATTTTCTCAGTACAACTTTGTATGGAATGCATAGGACACACACCTGATGC
TCTGTTCTTCCAGCCATGTGGGTTGTTTGTGTCCACATTAGGGCACTTACACCTCCATGT
GGAGACCATTTCTCTATGCAGTAGGAGACAAATAGAAATATTTTAATATTGGATTTATTT
TTTGGTATACAACCAGACAATAGTGCAGAAGATAGACTGGAGGGTTAGGTGCCAAGAAGT
CAAATTAAGGAGTCGTTGCAATAATCCATGAGGCCTGAAGAAGGCTTCAATTAAGAAAAG
AGAGAGAGCCAGAGAGAATGGAGTAGGGATTTAACATTTTCTAGGAAGATAAGGAAAAGA
ATGGCAATCCAGGAGAAAGAATGAGACACGGTTGCCAATAAACGTGATTAAGAAAAGGCA
TGCAGCACGAAATGAGCAGAACTTTTGCAAAACCTATATTTAAGGAATTAGCAACAATAA
CAAAAAGTAGTGGCTATCTTGAGAAGTTATCTCAAGGACAATTAACCAAGAGTTGATGA
GTTTCAGGATGTTGAGAATGAATACAGCTTTGGTCAGCGCAAATGCTGAAAGTAAGCTGA
```

FIG. 3

```
CATTTCTACCAAAGGTCACAGGGAAGTAGAAGCCCTGTGGTCTCCGTGTGCACAGAAAAC
TGAGAGCTTATTTGAAACAAATAAGAGCAAGAGAAAAAAGAGCCTTAAAGAAAAGGATT
TGATGGTTGACAACAGGCATATCAGAGAGTTTGCAAATAGCCCATTTGGATTTGCAAATT
TGGACCTCTTGCGATGTCTGTGAGTGTGATTTTATTAGAATGGTGGAGATGGAAGTCAAA
TTTTAATCGATTTAGGTGATGCGGATTGGGGAAATTGGGGAAACAAGTGTGGGCAATTTC
TGTTAAATAATTTGGTGACTAAGAGAAGGAGGGAGACAGGTTTCAATTTGAAGGGTATAA
GAGTTCAGAAAAGTACATTTGTTCATTTTTAAAAATAAATATGGAAGGAGGGAACCTGAG
TATATTTCTGTGGTGAAAGGTTAGAGAGAAGTGGAAATAGAATATCTAGAAAAGACCAGA
GCAAATTGCTGGTGTAATTTAAGAGGGGCAAAGTGTGCAGGTGAAAGTGTGAACCTTAGG
AGTCGGAAGCATGGACGCTAGGAGGTATAGACAAGAACTGGAGCAGGAGGTGGCTAGGCA
CTCTCCCCATTGGTGCCTTCTATTGCATTTATGAAGGGATCAGAGATATGCTGATGGTGA
GACAAGTAGAAATCTTGTAGGGAACTAGAGGAGAGAGAATACCAGAATTGGACTACTGGA
CACTTTGAATGCAGTAAGCACCTGCTTAAGATAAATACTCCCCTCACTAAGGAATCTCTG
AGAATGGTGGCTTTTTACAATATTGCACCTGGTGCTTATCACCTCACTCTTTATGAGTTT
CACAAATATTTAGTGAGCTCAGCCCATGTGCCTAGAACTATATCAAGGCCTAGTAGGTTT
TATAGGACAAGGAGAAGAGATGGCTCTTCAAGGAGCTTGGGCTTCTGTTCTGTCGGGTAG
TATTGGGCCAAGGAGTAGTTTCTTTCAGCCCATTTTCTTCTTCTATTGAACAGTATTTCA
TTGTCATATTATTCCATTTGCTGTTCATATGTGACTGCTTCTTGGTTGCATTGTACTTTC
CTGGGCGTGTTATCTATATTTTGTGAATGGAGAAAGGATCCATAATGACAGCATTTTGTT
CTTTCTCCCTATGCTTTCAAATAGTGTCAGGATGCTTATTTATCAGTGCTGCCTGCTGTG
AGCAGCTCTGTGCCAATTTAGCATCATCAGGAACAACTACATTAAGGTGATGGTCCCTGT
GCAAGATCCGTGAGCTCGTTCCACTAATTCATGAAAACATATTCATTTATTTTTAGCTAA
TAAAACGATCTTCAAACTGCTTGTTCAGGCATACATCACCAAAACATTTCCTATGTCTTT
AATGTTTTCAACCTTCATTATCTTTTCACTCCACTAATTTAGAATGTGGAGGGAAATCTC
TCAAATTTTATGAAATTATACTGCCATCATTTAACCTTTGCTATTATGCTGATTTATTTA
TTTATTCATTTATTTCTTTATGGCATAGGAATACATAATAAATAATGAGAATAGAGTTAG
CAACTTTTAAAAATAGAAAGTACTTACTAGAATAAAAATAGTTACCTGACAGAAAGTTTT
AAAAATAATCATTTCTTCTATTTATTCACTCCACATATGCTAAAAATTTTAGTGGAAACT
ACTGGTCCCGCTTCCTTCCCTGCAAAGCATCCATTTCCCTCCTTTGTCACTGGGAAGGAG
TCCTAGTTCCAGTGGGTTGAT
```

FIG. 3 CONT.

```
CTCACCTATGAGACCGCTTGGAGAAGTTGGAAGGGCCCAAGGGTATATCCAAAAATAACT
GACAAGCCCCTCAGCCTTCACCCAGGAGTTCCAGGATTGTCGTTCCCTGAGGCAAAGCTG
GCAAAGGTTTGGTGGCGGCAGCTAGGAGAAAGCACCTCTGGAACATCCCTCCTCGGTTTG
AAATTCTGTAAGATGAGCAGTGTCTCAGCAGGAAGGCTGAGTTCGCCAGCTGATAGGCAG
GCAGCTGACAGGCCGCAGAGCCGGGGTGCAGAGGATGACTCTGCTCGGGAAGTCTGCTGG
AGCTGCAGCTTGCCCAGGCTCTCTGCTCTGACACTCAGCATTTGCCTCCTCTTGAAACTG
ATCTCACCTTGTTTTCCACCTCCCCTCATCCACACAGAAGGTAGGATTTTTTTTTTTTTT
GAGGAAGATTAGCCCTGAGCTAACATCTGCTGCCAATCCTCCTCTTTTGCTGAGGAAGA
CTGGCCCTGAGCTAACATTCATGCCCATCTTCCTCTATGTTATATATGGGACACCTGCCA
CAGCATGGCTTGCCAAGCAGTGCTATGTCCGTACCCAGGATCCGAACCGGCAAACCCTGG
GCTGCCAAAGGGGAACGTGCACACTGAACCGATGCACCTCTGGGCTGGCCCCCATAAGTT
AGGATTTTTGATTTTCAAAATTTTTAAAATAAAATTATCTGTTGGGGCTGGCCCCGTGGC
CAAGTGGTTAAGTTCGCGCGCTCCGCTGCAGGCGACCCAGTGTTTCGTTGGTTCGAGTCC
TGGGTGCGGACATCGCACTGCTCATCAGACCACGCTGAGGCAGCGTCCCACATGCCACAA
CTAGAAGAACCCATAACGAAGAATACACAACTATGTACCGGGGGCTTTGGGGAGAAAAA
GGAAAAAATAAAATCTTTAAAAAAAAAATAAAAAATAAAAAATAAAATAAAATTATCT
GTTCATGTTTTTAACAGCCATAGAAATTATTAACTCCTAATTATAGAAACAGTGGAAAAC
AAAACCGTACAAAGAATAAAGGTGCCCAGAGACCCATAGTCACCAGACAAAGGCAACCAC
GTTTATATTTTGGCCTATTTGCTATCAGTCATTAATGTGTGTGTCTAGGCGCCCACATGT
GTGAATGCACATATTCCAACTTTAACACGACAAAATAAAACAAAGTTTGCACCCAAGTTA
AAGCCATGGTGGGTGACACTCAACGACTCACATTTGCAGTTAAGACCAAGGACTACCAGT
GGCCTTGCCTGGGCCACGTGACACTGCCGAGGGGCCGTTACAGTTCTAATTTACAGTTT
GGCTAAGCCAGGCGGCTTGGTGATAAGCACAGCTTGTTTATTTGTCTTTGATGGATGCCA
GGTGGATTGTGGTCAGACAATCTTCCTTCAGCAGCCTCAGCACTTTGCATCCACGGAGCT
AGCGTGAGGCCCTCCCCTGAGGAAAACGCAGGTCACACAATGAGCGCCCACAACAAAGGG
ACGGTCACAGTGGTGGCGGCACCAAACGAGGACAAAGAAGCGCTTGGGCGGAGAGGAAAG
AGGAAGAAAGCAGGGAGGGCCCAGGAGACGCCACCAGGCAGGCAGGTGGCCAGGCAAGCT
GACCAGCTTTGCTCTTGTGTTACAGGTTCACTCAGAGAACGAAGCTTTGGTGCACCTTT
TCATTACACTGCCTGTAAGGCTTCCAGGAATGAGTGCGGGCGATTTGCTGTGTTTTGACA
TTTTTTTCCCCTTTCTGAGAGCTGTCAGTTGAGAGGCAGTATCCTCTTGTGAGAGAGTTT
GGTGCCGGCTGCAAAATTAAAGGCAAGAAATAACCACAAATAAGAGAGCATGAGTGGCCA
GATATCTCTCAATCCTGATATGGGCTGTGGAAGGCCATGTGTGTTTATGTCCTCCCTCCA
GCTGGAGCCAAGAAGAGGCATCCGAGTGATGGCATCCAGAGGCTGCAGGAGGCAGCGGCC
TGTGGGGGTATAAAGGCAGTGGGATGACAGGGGCGTTCTGCTGGAAGCTGTACGAGGCC
CTTGTTGAAGCCAGTGAAGTGCACTGTGTCACCTCCAGTTTTCTTGGGGCTGGACTGGGC
TATCCATTGAAGAAATGGGGTGGAGAACCCAGGCTTAGTCATTTTTTTCCTCCCCAGTTT
CCGCTGGTTGTGGGCTGGAATGTGACATGTTGTTTTCTTTACTAATTGGGTCATAATTTT
AAAAAGCTGATGATCTCCTTTCCTTAAAGTACCAGGTCTCCATATCAAACCAGGGGAAAC
TGTGCCGTGGGGTTGCTGGTGAGTCTTGCTCCCTAGAAGCCCTGTAGGTGATCTGTGTCG
TCAGAAGACAGAAGGAGGAATGGGGGTTCCCTCCCTACTGCTCTGGAGAACTGTGCTCTA
GCAAGGGTGGAGCATGTTTCATTAAGTTTCCTGGGGGCAAACAGAGGGCCAAATGATAGA      ← ECA3F
TCAGTGTAGACGTAGTGTGACAGAGACCCAGGCAGA GCTCT|GCCTCCCGGCCTGCAGCAG
GGGCTCCCGACTTCCTTGAGTATGTGAATTTCCTCTTCAAACTCCAGAATCATTCAGAAC      ← ECA3xR
CTATGCTAGAGTGGGAGTAGCTGTTGACTGAGAAAACGAAAGATGATTCAAAAAATTATT
AAATATGCTTAAAACCATATTTGAGTACAACGAGAGGCACTCACAACTAGAAAACACAAC
TATGTACTGGGGGCTTTGGGGAGAAAAAGAAGAAAAAAGAAGATTGGTAATAGTTGTT
AGCTTAGGTACCAATCTTTTAAAAAAAAAGCATATTACTCGATAATCAAGTTATATAATG
GCATACAGTTAAAACCAAAGTTGTAAAGGGACCATCACAATCGTTTCTGCAATTGGACAA
ATACTCAACACACACCCCTTGTGTCGATTCATCCCACTCTTGGCAGTGCATCCTGTCGAT
GTGTACAATGGCAGCCATGATGCGTTCCTCCATTTCCTCAGGACTATGAGACTCTTGGTG
TATGCCCACGACATGTCAATGGTGTGATGACCTGAGCTCCCGGGTGGCTGCTGCTCCAGA
GTTAAGTCAATGTTTAAATAGAAAGCCCTACCCAGTGCCCTGGGATAGATTCATGAAAGA
ACTTCTGGACTGCTGGAAAATGAGGTTTCAAAGACTTCCTGAAGCTGTGGGAAAACCCTT
CAGTGTATCCTGACACTATGTTCTTCACACACACACACAGAGTTGGCATCTGTATTGA
TGTATCACAAAAGTCATGGGGGATCCCTTACACGTTCAATCACCACGTGTTGGTATTTGG
TGCCCCGTATATGGATGCTGTGAAGAATCACATTTTTAGTGAAATGAACACAGACTTATC
ATTGAATTTGAGACAACCTGCAAAGGCAACTTCGTCTTCTGTCTGAGTCTGAAAGCAGCA
```

FIG. 4

```
GCTGAAGTTTTATCGTTTTACCCCATCTGCCTCCATCAGAGCCTGCAGAGGGTGCAAGAA
GGTTTCATCTTCCATCGCTTATGGAGAAGGTGCCAGACCATGGTCTGAGGAACACAATAC
TCTCAGCCAGCCCTCTTTATGGACTCCTTGGGGCTCTGCTGAATGAGACAAAAATGATTC
CGTTTTCTTAAGACATGTGAAATGTAAGCACACACAAGTTGGTGCCTACTACATGTTGCT
AGTCATTGAGTAGTACATTTTTTTCTTCAAAGCGTTCAATTTTTTGAATCATCATGTACA
TACTGGCCAAAAACTACAAGTAACGCTTTTGAGTTAATTTGCATTTTTCTCATCACCAAA
GCATCTAAACACACCATAAAATAGTTAGACACATATACATCATACCACAGTAATGTGGCC
CTTTATAAAGTGGCATACTTTTTATAGCTACCTCCGCTGATCCTCAGAAAAATCCTGTAC
GATATGCACCATGATCCCCATTTTGCAGATAAGGAAACTGGGACTCAGAGAGACAGCCAC
TGATCAAGGTCTTGCACACAGCAGATTGTGGAACTAGGATTCCCTTCAGGCCTGGAAACC
CACAGCCGCTCCTACACCATGTGGCCTTCTCAAATAAGGAAAAACCTCTGATTTCTTAAA
ATAGTATTGTGCTATTATTCTCTTTTCTTGGTATATAAAAGTAAAGGTTTTAAATCTGGA
ATTTTGTTTGTTGTATTAGGTTGAAGTGTGCGAAACTGCTGATACTTTACCATTTCTGAC
CCTACGGTTCAACCTAATAGTTTTCTTCTCTGGGGGAAAGAAAGAAGGAAGGAAGGAAAG
AAGGAGAAAATGCAATGCATGAAAACAGAGAGCAATAAAAAGATCAAAAAGCACAGAAGG
AGGAAGAAAATGAGGGAAGGAAGAAGGTATAAGAAGAAATTAGAAATTACTAGTAAAGCT
TTGTCACTCTTTCTAAACTCTCCTGCCCTTCAGTTTCTTCCCCCACAGTCTTGGCTTTTA
CTGTCTATTGCCTTTGATCAGGATTTTCTCAGTCACCAGACTCCTTAAGTAATCAACAGA
GACCAACTGTATCATATTGTCTTTCATTCTTTATTTATTTTAAACAAGGATTGCGCAGAT
TTCTAGCCACCACCCCGAGGGGGTAAGAGGGAAGAAAAGATCGACAGAACAAAGTCTTGC
ATTTATTAGGACCGTCTAAATACGACTTTCTCTTCTCGGGGGAAAAACACTGGACCAAAA
CGAAATGCCCTCAATGTACAAATTTGTAGAAATGTAAAGTTAGCATACATTGAAGTTTCA
GATGAGAAACTTGACCTTAATGTTGAAAGAAGAGAGATGAGAAGACAAAAAAAATGAAAG
AAACCTTTTTAAATAAATAATTAGCTTGGAGATGATATAAAGTGTTTTCTAAATCAATCC
ATTCATAGGAAGAAATAAACACATTTGAACAATTTGATTAACACATGTGAATAACAAATG
ATAAAGCTAGGGAGCAGCTGAAGTCCTGCCACTGAAGACTTTAAGGGATAAATGCTCTCA
CCCCCTAATGCTGCCTCTGGA
```

FIG. 4 CONT.

METHOD FOR SCREENING FOR A TOBIANO COAT COLOR GENOTYPE

This utility patent application claims the benefit of priority in U.S. Provisional Patent Application Ser. No. 61/021,129 filed on Jan. 15, 2008.

TECHNICAL FIELD

The present invention relates to detection or screening for genotypes for coat color patterns. In particular, the present invention relates to screening for the genotype for the tobiano coat color pattern in horses. The method relies on detection of a chromosome inversion on horse chromosome 3 (ECA3).

BACKGROUND OF THE INVENTION

Tobiano is a white spotting pattern in horses caused by a dominant gene, Tobiano (TO). The tobiano color pattern of horses is highly valued and selected by many horse owners and breeders. Approximately 350,000 horses carrying TO are currently registered by the American Paint Horse Registry (APHA), but the pattern can also be found among several different horse, pony and draft breeds worldwide.

TO was previously shown to be genetically linked to the gene for Albumin(AL) (Trommershausen-Smith 1978). Later, an allelic association (linkage disequilibrium or LD) was discovered in which the chromosome possessing the TO allele usually possessed the Albumin (AL)-B and Vitamin D binding factor (GC)-S alleles (Bowling 1987). It is known that certain chromosome rearrangements, such as inversions, can create unusually strong LD by interfering with gamete formation, thus resulting in the formation of conserved haplotype blocks of alleles.

To explain the unusually high level of LD between the TO, AL and GC loci it was hypothesized that an inversion on ECA3 could be preventing recombination in this region (Bowling 1987). Several similar spotting patterns at the W locus in the mouse have been shown to be due to chromosomal rearrangements near the KIT (v-kit Hardy-Zuckerman 4 feline sarcoma viral oncongene homolog) gene. Two inversions, *Rump-white* (Stephenson et al., 1994) and *Sash* (Nagle et al., 1995), and four deletions, *Patch, 19h, 57,* and *Banded* (Nagle et al., 1994, Kluppel et al., 1997) occur within the 200 kb upstream of the KIT gene. All have been shown to disrupt the tissue-specificity or temporal expression of KIT during embryogenesis (Nagle et al., 1994; Kluppel et al., 1997; Hough et al., 1998; Berrozpe et al., 1999) rather than a coding sequence. The similarities between Tobiano and this particular group of mouse spotting patterns, previously demonstrated linkage of Tobiano and KIT horse chromosome 3 (ECA3) (Brooks et al., 2002) and the lack of a difference in the KIT cDNA of Tobiano horses (Brooks, 2006) all suggested that a nearby chromosomal rearrangement was the cause of the Tobiano allele. Initial efforts to detect an inversion using cytogenetic methods were unsuccessful (Raudsepp et al., 1999).

The rearrangement was finally demonstrated by one of the present inventors (Brooks, 2006; Brooks et al., 2007). Cytogenetic evidence showed that there was, indeed, a chromosome inversion on ECA3 near KIT which appeared to be completely associated with TO. No exceptions to the association of Tobiano with the inversion have been found and it is likely that the inversion has this effect by affecting regulation of the gene, KIT, during embryonic development. This conclusion is also based on observation of similar effects of mutation in KIT on mouse hair color.

The results of mapping several genes are shown in FIG. 1 and Table 1. In the left hand column of FIG. 1, a clear difference can be seen in the distance between KDR (red) and KIT (orange) when comparing the ECA3 from non-spotted horses and the ECA3 bearing TO. The center set of images shows three markers (ALB, Clock, and GABPB1) with different relative orders on each chromosome. The right column shows results from FISH mapping a bacterial artificial chromosome (BAC) 558 which crosses the distal breakpoint (green). On ECA3 from non-spotted horses, hybridization occurred at a single location, while on the chromosome with Tobiano two distinct locations were labeled with the single probe.

TABLE 1

FISH Markers used in this study in their relative linear order on ECA3.

| Marker | CHORI-241 BAC Clones | HSA | ECA | Relation to Inversion | Sequence Source |
|---|---|---|---|---|---|
| GABRB1 | 49:M13 | 4q046.8mb | 3q21 | Telomeric | UCSC Consensus |
| TEC | 38:G1 | 4q047.9mb | 3q21 | Telomeric | UCSC Consensus |
| PDGFRA | 23:F11 | 4qos4.9 | 3q21 | Telomeric | UCSC Consensus |
| KIT e21 | 90:F8 | 4q055.447mb | 3q21 | Telomeric | Genbank #AY874S43 |
| Intergenic Seq. "558" | 102:M1 | 4q055.558mb | 3q21 | At Breakpoint | UCSC Consensus |
| KDR5'Ue1 | 129:04 | 4q055.787mb | 3q21 | Within | UCSC Consensus |
| KDR | 127:D23 | 4q055.7mb | 3q21 | Within | UCSC Consensus |
| Clock | 11:A9 | 4q056.2mb | 3q21 | Within | Murphy et al. 2007 |
| ALB | 21:KS | 4q074.6mb | 3q14. | Within | Genbank #AY008769 |
| CCNI | 99:89 | 4q078.4mb | 3q14. | Within | Chowdhary et al. 2003 |
| ENOPH1 | 69:C10 | 4q083.7mb | 3q13 | Within | Genbank #cxs03024 |
| WDFY3 | 44:L24 | 4q085.9mb | 3q13 | Within | Genbank #CX599384 |
| HSD17B11 | 105:819 | 4q088.7mb | 3q13 | Within | Chowdhary et al. 2003 |

TABLE 1-continued

FISH Markers used in this study in their relative linear order on ECA3.

| Marker | CHORI-241 BAC Clones | HSA | ECA | Relation to Inversion | Sequence Source |
|---|---|---|---|---|---|
| PDLIM5 | 19:G11 | 4q095.7mb | 3q13 | Within | UCSC Consensus |
| ADH1C | 189:L20 | 4q100.6mb | 3q13 | Centromeric | Genbank# AF134056 |

Since the presence of the tobiano pattern can increase value, horse breeders prefer to use breeding stock which are homozygous for TO, e.g., those which have inherited a copy of the gene from both parents, and will always transmit the gene to their offspring. The cytogenetics test requires freshly collected cells and is expensive to conduct. In place of a cytogenetic test for Tobiano, associative tests have been used to predict homozygosity for Tobiano. As described above, the Tobiano gene was associated in horse populations with particular gene-alleles or SNPs. Specifically, most but not all horses with the Tobiano gene also possessed the B allele for AL and the S allele for GC. Likewise, most but not all horses with the Tobiano gene also possessed the KM1 single nucleotide polymorphism of the gene KIT. Known methods for detecting genetic markers associated with the Tobiana genotype include detection of these nearby genetic markers using biochemical typing or molecular DNA tests. However, biochemical typing methods require freshly obtained biological samples. Furthermore, both biochemical and molecular gene detection methods also produced false positive and false negative reactions because they are associative with the tobiano trait and not actually responsible for the trait (Duffield and Goldie, 1998; Brooks et al., 2002).

Until present, there have been no precise and cost effective methods to identify all horses homozygous for TO. While the inversion can be detected using cytogenetic studies and fluorescence in situ hybridization (FISH) of DNA probes for genes in the region, this is an expensive and time-consuming procedure. There remains a need in the art for a methods for identifying animals bearing the Tobiano genotype which are effective, rapid, and which further can be performed effectively on stored samples of varying type, to obviate the need for acquiring fresh genetic material.

SUMMARY OF THE INVENTION

The above-mentioned and other problems are solved by applying the principles and teachings associated with the presently described method for screening for a genotype for a tobiano coat color pattern in an equine animal. In one aspect, the method includes the steps of obtaining a sample containing a nucleic acid from the horse, and analyzing the nucleic acid for the presence of DNA sequence characteristic of an inversion in a chromosome ECA3q. The inversion spans a large region of ECA3, from q13 to q21. One inversion breakpoint lies between the KIT gene and the KDR gene (distal or telomeric breakpoint) while the inversion breakpoint nearest the centromere lies between the ADH1D gene and the UNC5C gene (proximal or centromeric breakpoint). As will be set forth more fully below, the presence of the chromosomal inversion indicates that the equine animal possesses the Tobiano coat color pattern genotype.

In particular, the chromosomal inversion may be defined by addresses in the equine genome. With reference to the equine genome (EquCab2, available on the University of California Santa Cruz Genome Browser, Genome Bioinformatics Group, Center for Biomolecular Science and Engineering, UCSC) the telomeric breakpoint has been identified as between nucleotides 3:41925230-4192523 1 of EquCab2. The centromeric breakpoint has been identified as between nucleotides 3: 77663330-77663331 of EquCab2. Those breakpoints, along with the 5 kb surrounding those addresses, are set forth in FIGS. 3 and 4 (see SEQ ID NO:13 and SEQ ID NO: 14).

In one embodiment, the nucleic acid is analyzed for the presence of the distal chromosomal inversion by the steps of hybridizing to the nucleic acid three probes or primers having the sequences set forth as SEQ ID NO:8, SEQ ID NO:9, and SEQ ID NO:10, and deriving an amplification product from those primers. Presence of the chromosomal inversion, and therefore the Tobiano genotype, is indicated by an amplification product having a 209 bp nucleic acid sequence set forth herein as SEQ ID NO:11. An amplification product of 152 bp in length (SEQ ID NO:12) denotes a chromosome lacking an inversion in that region. Different sets of DNA primer sequences may be designed to amplify DNA fragments of the same or different sizes, but the principal accomplishment is the same as long as the primers flank either of the inversion sites found to accompany the Tobiano gene or to occur within the region to detect genetic markers associated with the inversion. The chromosome inversion, or the DNA sequence associated with the inversion, may be detected by any suitable method of DNA analysis, including without limitation, by gel electrophoresis, Southern blotting and specific DNA sequence analysis. Advantageously, the presently described method may be performed on any suitable fresh or stored sample containing a nucleic acid, including without limitation a cell, a tissue, a hair follicle, buccal swab, serum, plasma, and other biological materials derived from an individual.

These and other embodiments, aspects, advantages, and features of the present invention will be set forth in the description which follows, and in part will become apparent to those of ordinary skill in the art by reference to the following description of the invention and referenced drawings or by practice of the invention. The aspects, advantages, and features of the invention are realized and attained by means of the instrumentalities, procedures, and combinations particularly pointed out in the appended claims. Various patent and non-patent references are discussed herein. Unless otherwise indicated, any such references are incorporated in their entirety into the present disclosure specifically by reference.

BRIEF DESCRIPTION OF THE DRAWINGS

The accompanying drawings incorporated in and forming a part of the specification, illustrate several aspects of the present invention, and together with the description serve to explain the principles of the invention. In the drawings:

FIG. 3 shows the sequences surrounding the proximal (centromeric) breakpoint of a chromosomal inversion in Tobiano ECA3, with primer binding sites and the region of the breakpoint shown in double underlining, and the breakpoint address identified by a vertical line (see SEQ ID NO: 13);

FIG. 4 shows the sequences surrounding the distal (telomeric) breakpoint of a chromosomal inversion in Tobiano ECA3, with primer binding sites and the region of the breakpoint shown in double underlining, and the breakpoint address identified by a vertical line (see SEQ ID NO: 14);

DETAILED DESCRIPTION OF THE ILLUSTRATED EMBODIMENTS

In the following detailed description of the illustrated embodiments, reference is made to the accompanying drawings that form a part hereof, and in which is shown by way of illustration, specific embodiments in which the invention may be practiced. These embodiments are described in sufficient detail to enable those skilled in the art to practice the invention. Also, it is to be understood that other embodiments may be utilized and that process, reagent, software, and/or other changes may be made without departing from the scope of the present invention.

EXAMPLE 1

Figure 1:
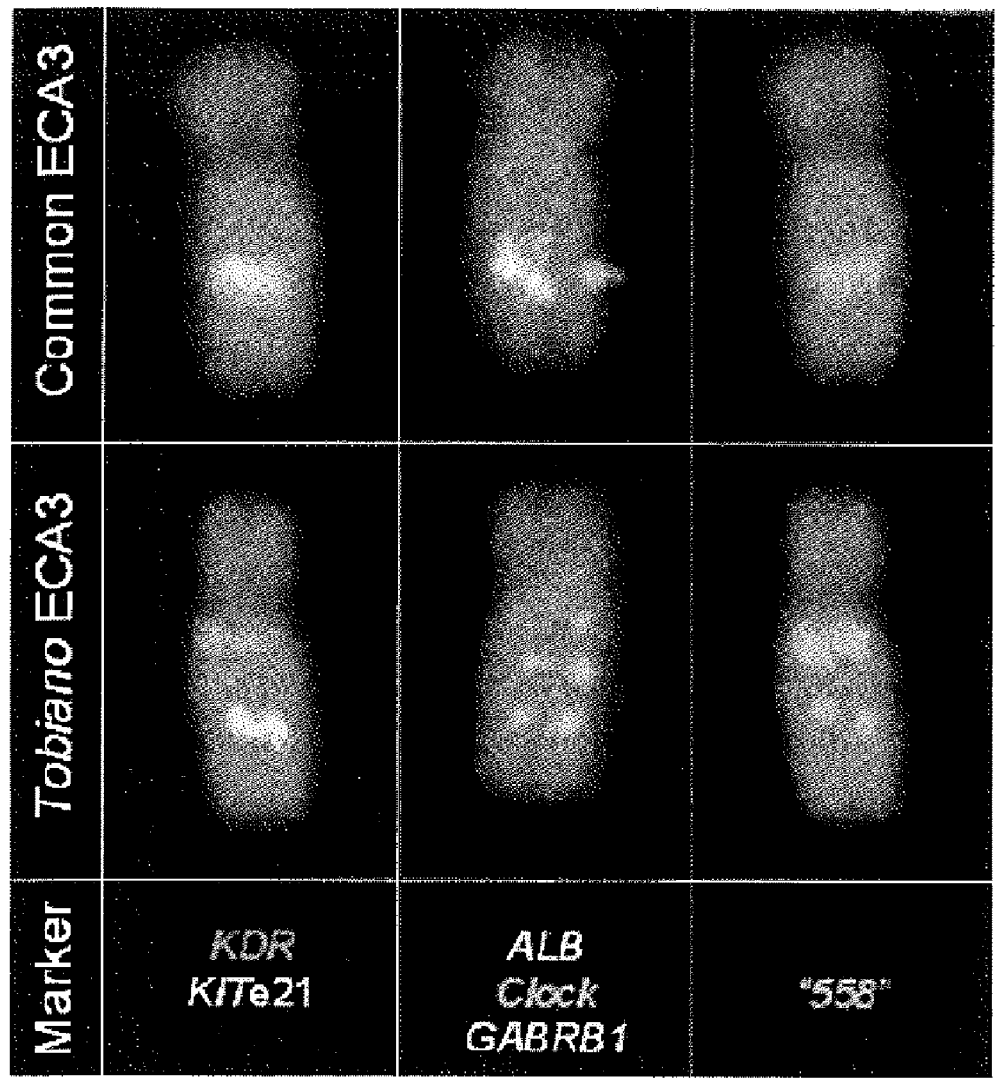
FIG. 1 compares fluorescence in situ hybridization (FISH) analyses of common and Tobiano ECA3 chromosomes.
Figure 2:
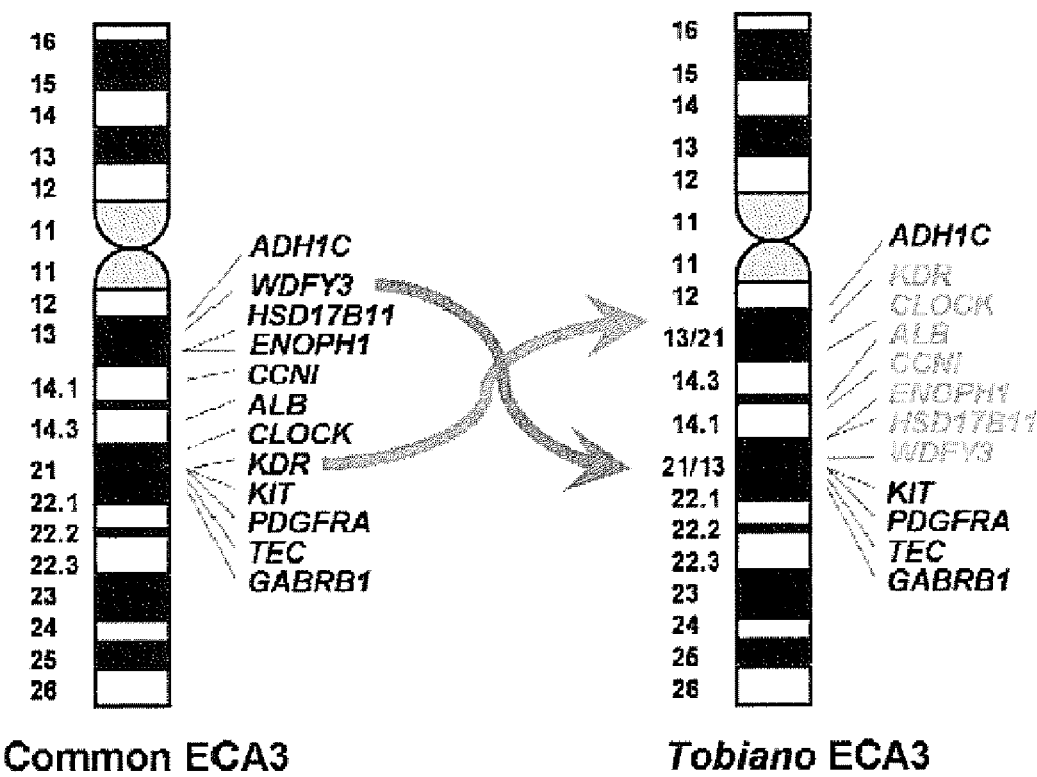
FIG. 2 schematically depicts the positions of various genes located on equine ECA3 in common (non-Tobiano) ECA3 chromosome and in the Tobiano ECA3 chromosome having an inversion.

As noted above with respect to genetic markers useful for cytogenetic demonstration of the inversion, one BAC clone (558) mapped to a single location, near KIT, on chromosomes without TO but at two locations, associated with the inversion sites, on chromosomes possessing TO (FIG. 1). This demonstrated that BAC 558 included one of the two sites at which the inversion occurred. Therefore, it was possible to sequence BAC 558 to identify the distal breakpoint for the inversion site.

The homologous human genome position of the end sequences for BAC 558, shown in FISH experiments to contain the distal breakpoint of the inversion, was determined by searching the database available at the Horse Genome Project web site (Leeb et al., 2006). Within these endpoints regions of high conservation approximately 3-5 kb apart were selected based on the conservation track of the UCSC Genome Browser (Kent 2002). The human sequence for these conserved areas was then used to find a corresponding horse sequence from the trace files submitted to the Entrez Trace Archive using a Discontiguous Megablast (NeBI, 2006). The relative position of these trace files was confirmed by comparing them back to the human genome using the BLAT search on the UCSC Genome Browser. Primers were designed for each individual trace using the Vector NTI software package (Invitrogen, Carlsbad Calif.).

Primer pairs first optimized to amplify the small product contained in the trace file were then used with the appropriate primer from the next trace to create a product containing the sequence between the two distant trace files. Thirty seven primer pairs were created, and amplification of the intervening sequence was confirmed using DNA from a known TO/TO horse until a primer pair was found where amplification was successful in the non-Tobiano but not the TO/TO horse, indicating that the primer pair had been separated by the inversion. That primer pair is set forth in Table 2.

TABLE 2

Primers used to screen for the distal ECA3 inversion breakpoint.

| Trace File Accession # | Human Address (Chr4: in Mb) | |
|---|---|---|
| | | Forward Primer 5'-3' |
| 1250295308 | 55400840 | CTGCCTCCATCAGAGCCTGCA (SED ID NO: 1) |
| | | Reverse Primer 5'-3' |
| 1378686387 | 55402968 | TGGAGGTGACACAGTGCACTTCACT (SEQ ID NO: 2) |

This set of primers was used to screen animals for the presence of the chromosomal inversion. Absence of a PCR product indicated that the primers were separated by the inversion. This test required use of a positive PCR control fragment, and only detected homozygosity.

The sequence between the two trace files identified was then determined. The sequence located at the distal breakpoint in a TO/TO horse was determined by genome walking using the APAgene GOLD Genome Walking Kit (BioS&T, Ontario Canada) following the manufacturers directions. Briefly, several rounds of nested PCR were performed using sequence specific primers for the known sequence and universal primers to extend the amplified product in to unknown sequences for which specific primers could not be designed. The primers used were as follows:

BPFa:
(SEQ ID NO: 3)
GAT CAG TGT AGA CGT AGT GTG ACA GAG ACC CAG G;

BPFb:
(SEQ ID NO: 4)
GGC AAA CAG AGG GCC AAA TGA TAG ATC AGT GTA GAC;

BPFc:
(SEQ ID NO: 5)
TGT GCT CTA GCA AGG GTG GAG CAT GTT TCA TTA AG.

The resulting PCR product was directly sequenced using an ABI310 (Applied Biosystems, Foster City, Calif.) following the manufacturers standard protocol for chemistry and conditions. Fifty-two bases of horse sequence beyond the inversion breakpoint were generated (with reference to Genbank Accession #EF442014) and used by Megablast of the Trace Archive to pull trace files containing that sequence NCBI, 2006). The position of these trace sequences relative to the human genome was determined using the BLAT function of the UC8C Genome Browser. The equine sequence encompassing both breakpoint boundaries was determined by assembling these trace files with the ContigExpress function of VectorNTI (see FIGS. 3 and 4). The Genbank accession numbers of the trace files used to create the assembly were:

Centromeric end: 1231203553,1288909375, 1248629699, 1411501757, 1204375030, 1276786693, 1248632879, 1419986588,1286709380,1387598584, 1273872762, 1207301472, 1417784590, 1326270692; and Telomeric end: 1250295308, 1199900846, 1465783553, 1304105951, 1258859536, 1227749574, 1248814034, 1213964577, 1378686387.

The DNA sequence at the site of the inversion was then identified by sequence walking using DNA from a homozygous (TO/TO) horse as a template (Genbank Accession #EF442014). This sequence, once extended using an alignment of the available equine whole genome sequence trace files from the trace archive at NCBI, was used to design primers that amplify PCR products of unique sizes for each of the inverted and non-inverted chromosomes. The sequences of the assembled contigs for the common (non-Tobiano) and Tobiano sequences are set forth as SEQ ID NO: 6 and SEQ ID NO: 7, respectively.

Figure 5:
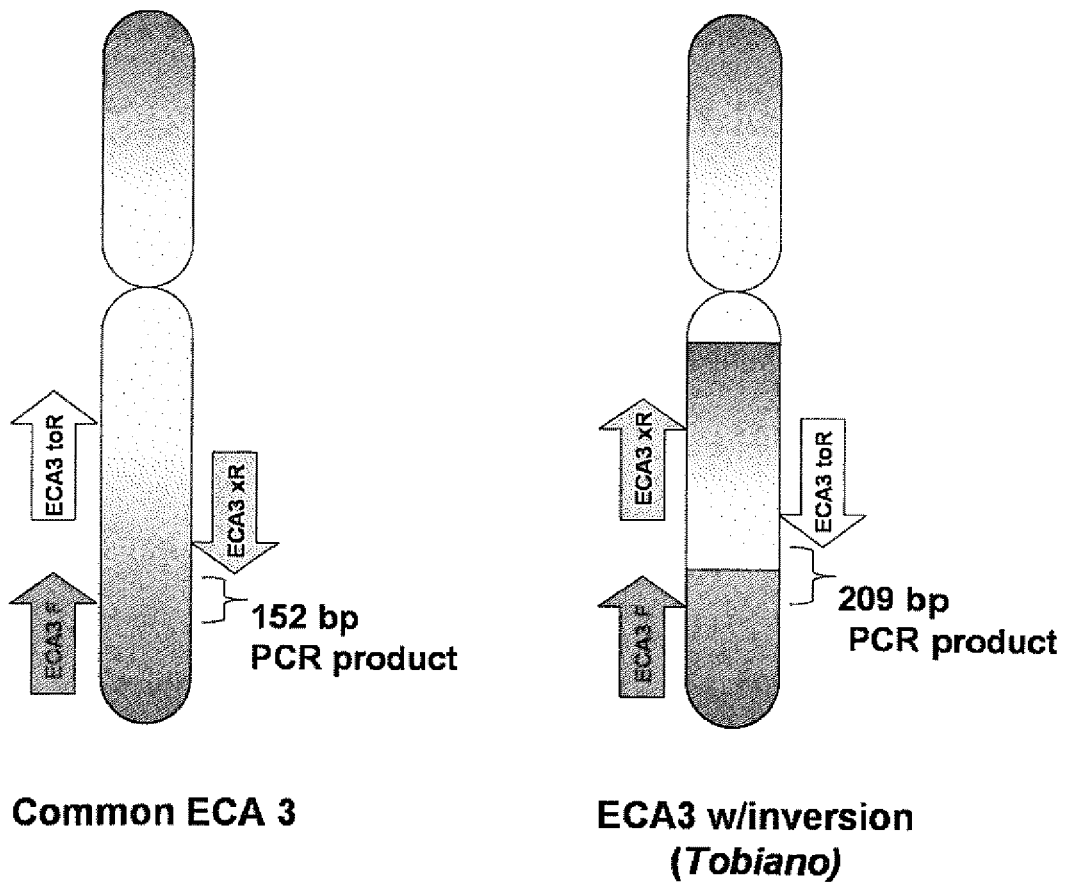
FIG. 5 schematically depicts a primer strategy used to detect the inversion in ECA3.

For allele identification by PCR, all primers were designed using Vector NTI. A common forward primer was first designed using the sequence just outside of the telomeric end of the inversion. Then a primer specific for the adjoining sequence within the inverted region in the common chromosome and a primer specific for the tobiano inversion were designed to produce two different size PCR products of 209 bp (SEQ ID NO:11) and 152 bp (SEQ ID NO:12), respectively (see FIG. 5). The primer sequences used were as follows:

```
ECA3-F:
                                      (SEQ ID NO: 8)
TGA TAG ATC AGT GTA GAC GTA GTG TGA CAG AGA C;

ECA3xR:
                                      (SEQ ID NO: 9)
AAC AGC TAC TCC CAC TCT AGC ATA GGT TC;

ECA3toR:
                                      (SEQ ID NO: 10)
TTC ACC ACA GAG TAT CCA ATT ATG TCT TTC ACA TAA
TGC.
```

Figure 6:
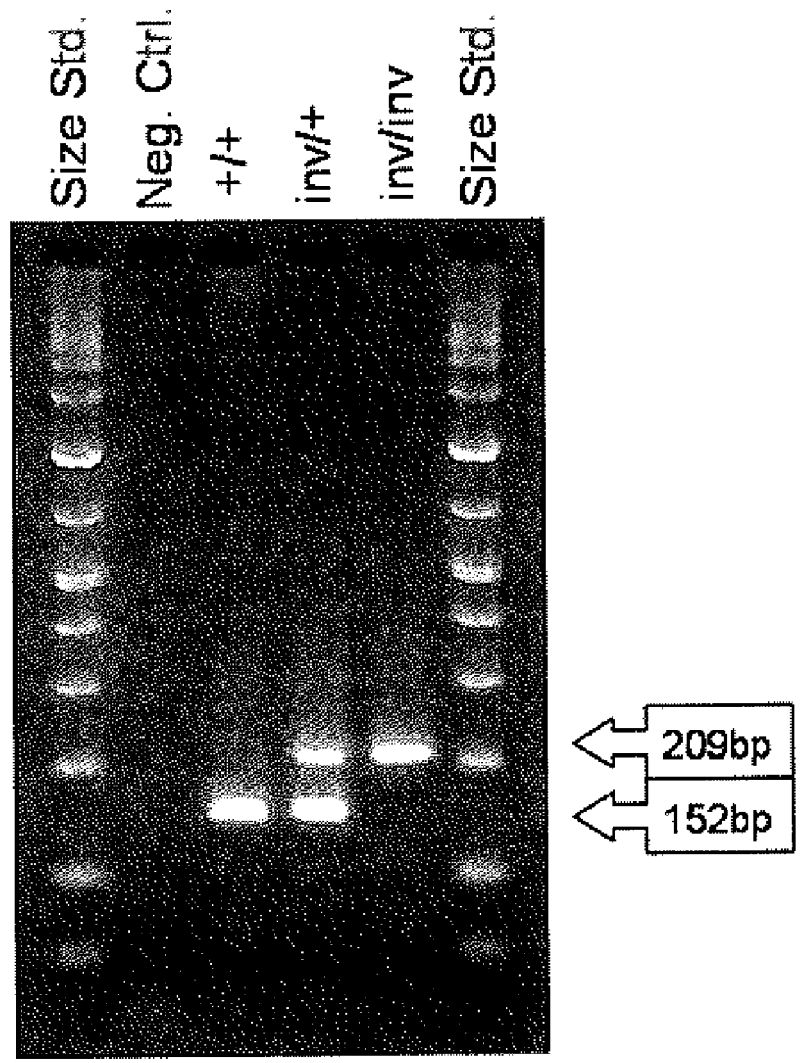
FIG. 6 shows a representative result for the present method for detecting a chromosomal inversion in ECA3 by PCR, with amplification products detected by gel electrophoresis and ethidium bromide staining, with the marked 152 bp product being indicative of the common (non-Tobiano) ECA3 and the 209 bp amplification product being indicative of the ECA3 inversion (Tobiano).

PCR was preformed using FastStart polyinerase (Roche, Indianapolis Ind.) following in a 10 µL volume using 25 ng extracted DNA or 2 µL of hair lysate prepared using 5-7 hair bulbs according to the method previously published by Locke et al., 2002. Primer concentrations were adjusted as follows to produce two bands of approximately equal intensity: 0.5 uM ECA3-F primer (1 µL of 5 uM dilution), 0.325 µM ECA3xR primer (0.65 µL of 5 µM), 0.175 µM ECA3toR primer (0.35 µL of 5 µM). All other reagents were used following the manufacturers recommendations. Thermocycling was performed in a PTC-200 thermocycler (MJ Research Inc., Boston, Mass.) with an annealing temperature of 57° C. and 20 s extension time for 35 cycles. Products were visualized by electrophoresis on a 3% agarose gel after staining with ethidium bromide (FIG. 6). Presence of the 152 bp PCR product (SEQ ID NO:12) indicated the horse carried at least one copy of the common chromosomal arrangement. Likewise, presence of the 209 bp product (SEQ ID NO:11) was indicative of the presence of the inversion.

The chromosomal inversion has been defined by identifying addresses in the equine genome. With reference to the equine genome EquCab2, available on the UCSC Genome Browser, Genome Bioinformatics Group, Center for Biomolecular Science and Engineering, University of California Santa Cruz, the telomeric breakpoint is located between nucleotides chr3:41925230-41925231 of EquCab2. The centromeric breakpoint is located between nucleotides chr3: 77663330-77663331 of EquCab2. Those breakpoints, along with the 5 kb surrounding those addresses, are set forth in FIGS. 3 and 4 (see SEQ ID NO:13 and SEQ ID NO: 14). The 5 kb nucleotides surrounding the centromeric and telomeric breakpoint addresses are set forth in SEQ ID NO:13 and SEQ ID NO:14, respectively, as derived from the publically available ECA3 (EquCab2, UCSC Cenome Browser). These sequences are depicted also in FIGS. 3 and 4, respectively, with the breakpoints indicated by a vertical line and the binding sites for the primers ECA3-F (SEQ ID NO: 8), ECA3xR (SEQ ID NO: 9), and ECA3toR (SEQ ID NO: 10) indicated by underlining and by arrows extending from the respective primer designators.

EXAMPLE 2

To further evaluate the ability of the PCR method set forth in Example 1 to detect the chromosomal inversion, additional stored samples were obtained for molecular marker studies and DNA sequencing. Previously banked DNA samples from 58 Thoroughbreds (non-tobiano) and 121 tobiano horses of various breeds were selected from samples available at the Immunogenetics and Genomics Laboratory, University of Kentucky. Photographs, pedigree and registrations were examined for all tobiano horses in order to verify presence of the tobiano pattern. Specifically, these horses possessed large white patches that crossed the dorsal midline and had smooth borders. None of the total 179 horses were related as siblings or half-siblings. All tobiano horses had at least one tobiano patterned parent. The breeds of horses evaluated, and the results of the present method for detecting the chromosomal inversion, are provided in Table 3.

TABLE 3

Breeds of Horses tested for the ECA3 inversion.

| Breed | inv/inv | inv/+ | +/+ |
|---|---|---|---|
| American Miniature Horse | 2 | 3 | |
| American Paint Horse | 16 | 53 | |
| Arab/Pinto | | 5 | |
| Draft and Draft Cross | 2 | 4 | |
| Icelandic Horse | | 1 | |
| Missouri Fox Trotter | | 2 | |
| Pinto | | 6 | |
| Saddlebred | | 2 | |
| Shetland Pony | 1 | 3 | |
| Spotted Saddle Horse | | 3 | |
| Tennessee Walking Horse | 2 | 12 | |
| Thoroughbred (non-Tobiano) | | | 58 |
| Welsh Cross | 2 | 2 | |
| Total | 25 | 96 | 58 | 179 |

Of 121 horses with the tobiano pattern, all possessed the PCR amplified 209 bp DNA fragment (SEQ ID NO:11) consistent with the inversion. These horses included the following breeds: American Miniature (5), American Paint (69), Arabian (5), draft and draft crosses (6), Icelandic Horse (1), Missouri Fox Trotter (2), Saddlebred (2), Shetland Pony (4), Spotted Saddlehorse (3), Tennessee Walking Horse (14), the Welsh Cross (4) (Table 2). These breeds encompass a wide range of historical breed origins. None of 58 control Thoroughbred horses without the tobiano pattern possessed the inversion, including 3 that carried the KM1 marker.

The tobiano pattern is usually, but not always, associated with the haplotype possessing alleles ALB-B, GC-S and KMI. Therefore, horses with other haplotypes were tested for the presence of the inversion. These haplotypes and their association with the inversion are shown in Table 4. The inversion was present with alleles ALB-A, GC-F and KMO, in addition to the alleles from the most frequent haplotype. Therefore, it is likely that the Tobiano inversion event occurred on a chromosome possessing ALB-B, GC-S and KA1, followed by rare mutations or genetic recombination resulting in new haplotypes possessing TO.

TABLE 4

Haplotype association of genetic markers for Albumin (ALB), Vitamin D binding Protein (GC), KIT intron 13 SNP (KM) with TO and the ECA3 inversion.

| Horse ID# | Breed | Phenotype | AL | Gc | KM | ECA3 Inversion | TO Haplotypes (AL/Gc/KM) |
|---|---|---|---|---|---|---|---|
| 78 | APHA | TO | A | F | 1/0 | inv/+ | A/F/unknown |
| 351 | APHA | TO | B | F/S | 1/1 | inv/inv | B/F/1, B/S/1 |
| 481 | Draft cross | TO | B | F | 1/1 | inv/+ | B/F/1 |
| 480 | Welsh cross | TO | B | S | 010 | inv/inv | B/S/0 |
| 479 | Welsh cross | TO | B | S | 1/0 | inv/inv | B/S/1, B/S/0 |

EXAMPLE 3

The experiment set forth in Example 1 is repeated using PCR primers designed to amplify the centromeric site of the inversion for those horses with the Tobiano inversion. The PCR and gel electrophoresis conditions are as set forth in Example 1. In this case, the primers would flank the inversion site shown in FIG. 3. Primers ECA3xR (SEQ ID NO:9) and ECA3toR (SEQ ID NO:10) are used, along with a primer ECA3Fc (SEQ ID NO:15; FIG. 3) having a complementary sequence ATGTGCAGTACTCATAATACATTC. Use of this primer combination produces a DNA fragment of approximately 261 basepairs for chromosomes without the inversion and a fragment size of approximately 204 basepairs for chromosomes possessing the inversion.

EXAMPLE 4

The inversion can be inferred using the technique of restriction fragment length analysis (RFLP). In this approach: 1) DNA fragments are produced including one or both of the chromosome inversion sites; 2) the DNA is digested with restriction enzymes; and 3) the fragments are analyzed by gel electrophoresis for fragment length differences denoting the presence or absence of chromosomes with inversions. Any DNA restriction enzymes recognizing sites on both sides of the inversion as described herein is effective in detecting the presence of fragments characteristic of the presence of the inversion. Experimental techniques for RFLP analysis are as set forth in Molecular Cloning, A Laboratory Manual, Sambrook and Russell, 2001, Chapter 5.

EXAMPLE 5

Southern blotting (see Chapters 5-6, Sambrook and Russell, 2001) is a method of hybridizing DNA fragments to chromosomal DNA fragments in order to visualize the presence of homologous fragments. In this method, chromosomal DNA is fragmented in a method that produces reproducible cuts, usually with DNA restriction enzyme. The fragments are separated based on length by gel electrophoresis. Subsequently, DNA, called a probe, homologous to DNA from the same region is labeled such that it can be visualized and subsequently hybridized to the chromosomal DNA. Differences in DNA fragment lengths based on the presence or absence of the inversion can be detected by visualizing differences in the size of fragments hybridizing to the probe.

EXAMPLE 6

As shown in FIGS. 3 and 4, the DNA sequences surrounding the inversions are unique to horses possessing the chromosome inversion. DNA sequencing through the inversion site would effectively demonstrate the presence or absence of the normal or inverted chromosome fragment.

The presence of a chromosomal rearrangement in ECA3 of animals bearing the Tobiano coat color genotype is now demonstrated, and a method is set forth for detecting the Tobiano coat color genotype in an equine animal, based on detection of the large, paracentric inversion in equine chromosome 3. This inversion described in the foregoing description does not disrupt the coding sequence of any known genes; consequently it is not readily apparent how this may cause the tobiano phenotype. However, without being restricted to any particular theory, the inversion may disrupt conserved non-coding or regulatory regions of the KIT gene, similar to what has been observed in the murine Bump-white (Stephenson et al. 1994) and Sash (Nagle et al. 1995) inversions. Both of these inversions disrupt regulatory elements 5' to the KIT gene and lead to inappropriate temporal and spatial expression in the embryo (Duttlinger et al. 1993; Nagle et al. 1995). Regulatory gene elements that form a loop structure, like enhancers, insulators, and locus control regions, can bind sequences both upstream and downstream of their target gene (Maston et al. 2006). Regulatory elements such as these, encompassing the KIT gene from the intergenic regions upstream to those downstream, could explain the similarities in appearance between the Tobiano phenotype, which is a rearrangement beyond the 3' end of KIT, and the Rump-white and Sash mouse phenotypes, which are both rearrangements of the 5'end of KIT.

Horses with Tobiano are normal and healthy, suggesting that this chromosome rearrangement is not associated with deleterious health effects. Presence of the inversion among breeds of diverse origins indicates that it predates divergence of these horse and pony breeds. So far there no exceptions have been found for the association of this inversion with the tobiano phenotype, strengthening the hypothesis of homogeneity for the phenotype and genotype. The presently-described PCR-based method for identifying the Tobiano genotype will be useful to breeders interested in finding breeding stock homozygous for tobiano since carriers and Tobiano homozygotes are usually phenotypically indistinguishable. The method can be utilized on any material with DNA, and does not require viable cells. The method thus advantageously does not require freshly obtained genetic material, and even more may be performed on a variety of biological sample types such as hair, with the proviso that the biological sample contains DNA. Hence, more individuals can be subjected to routine screening than would be practical using a more expensive and time-consuming assay such as the FISH method.

One of ordinary skill in the art will recognize that additional embodiments of the invention are also possible without departing from the teachings herein. This detailed description, and particularly the specific details of the exemplary embodiments, is given primarily for clarity of understanding, and no unnecessary limitations are to be imported, for modifications will become obvious to those skilled in the art upon reading this disclosure and may be made without departing from the spirit or scope of the invention. Relatively apparent modifications, of course, include combining the various features of one or more figures with the features of one or more of other figures.

REFERENCES

Duffield, DA, Goldie PL (1998) Tobiano Spotting Pattern in Horses: Linkage of To With A1A and Linkage Disequilibrium. Journal of heredity 89: 104-106.

Brooks SA, Lear TL, Adelson DL, Bailey E. (2007) Characterization of the breakpoints of a chromosome inversion associated with the tobiano white spotting pattern in horses. Plant and Animal Genome Conference XV, P599.

Berrozpe, G., Timokhina, I., Yukl, S., Tajima, Y., Ono, M., Zelenetz, A., and Besmer, P., (1 999). The W(sh), W(57), and Ph KIT expression mutations define tissue~specific control elements located between −23 and −154 kb upstream of KIT. Blood 94, 2658-2666.

Bowling, A., 1987. Equine linkage group II: phase conservation of To with A1B and GeS. $J$ $Hered$ 78(4),248-250.

Brooks, S., Terry, R., and Bailey, E., 2002. A PCR-RFLP for KIT associated with tobiano spotting pattern in horses. Anim Genet 33(4), 301-303.

Brooks, S, 2006. Studies of Genetic Variation at the KIT Locus and White Spotting Patterns in the Horse, Ph D. dissertation. University of Kentucky, Lexington Ky. USA.

Chowdhary, B., Raudsepp, T., Kata, S., Goh, G., Millon, L., Allan, V., Piumi, F., Guerin, C., Swinburne, J., Binns, M., et at., 2003. The first-generation whole-genomne radiation hybrid map in the horse identifies conserved segments in human and mouse genomes. Genome Res 13(4), 742-751.

Duttlinger, R., Manova, K., Chu, T., Gyssler, C., Zelenetz, A., Bachvarova, R., and Besmer, P. 1993. W-sash affects positive and negative elements controlling c-kit expression: ectopic c-kit expression at sites of kit-ligand expression affects melanogenesis. Development 118(3), 705-717.

Hough, R., Lengeling, A., Bedian, V., Lo, C. and Bucan, M., (1998). Rump-white inversion in the mouse disrupts dipeptidyl aminopeptidase-like protein 6 and causes dysregulation of KIT expression. Proc Natl Acad Sci 95, 13800-13805.

Karolchik, D., Baertsch, R., Diekhans, M., Furey, T., Hinrichs, A., Lu Y., Roskin, K., Schwartz, M., Sugnet, C., Thomas, D.,et at., 2003. The UCSC Genome Browser Database. Nucleic Acids Res 31(1), 51-54.

Kent, W., 2002. BLAT—The BLAST-Like Alignment Tool, http://genome.ucsc.edulcei-bin/hgB lat?command=start.

Kluppel, M., Nagle, D., Bucan, M., and Bernstein, A., (1997) Long-range genomic rearrangements upstream of KIT dysregulate the developmental pattern of KIT expression in $W^{57}$ and $W^{banded}$ mice and interfere with distinct steps in melanocyte development. Development 124, 65-77.

Lear, T., Brandon, R., Piumi, F., Terry, R., Guerin, G., Thomas, S., and Bailey, E., 2001. Mapping of 31 horse genes in BACs by FISH. Chromosome Res 9(3), 261-262.

Leeb, T., Vogl, C., Zhu, B., de Jong, P., Binns, M., Chowdhary, B., Scharfe, M., Jarek, M., Nordsiek G., Schrader F., and Blocker H., 2006. A human-horse comparative map based on equine BAC end sequences. Genomics 87(6), 772-776.

Locke, M., Penedo, M., Bricker, S., Millon, L., and Murray, J., 2002. Linkage of the grey coat colour locus to microsatellites on horse chromosome 25. Anim Genet 33(5),329-337.

Maston, G., Evans, S., and Green, M., 2006. Transcriptional Regulatory Elements in the Human Genome. Annu Rev Genomics Hum Genet 729-759.

Murphy B., Lear T., Adelson D., and Fitzgerald B., 2007. Chromosomal assignments and sequences for the equine core circadian clock genes. Animal Genetics 38(1), 84-85.

Nagle, D., Martin-DeLeon, P., Hough, R. and Bucan, M., 1994. Structural analysis of chromosomal rearrangements associated with the developmental mutations Ph, $W^{19H}$, and Rw on mouse chromosome 5. Proc Natl Acad Sci 91,7237-7241.

Nagle D., Kozak C., Mano H., Chapman V., and Bucan M., 1995. Physical mapping of the Tec and Gabrb 1 loci reveals that the $W^h$ mutation on mouse chromosome 5 is associated with an inversion. Hum Mol Genet 4(11),2073-2079.

Raudsepp T., Kijas J., Godard S., Guerin G., Andersson L., and Chowdhary B., 1999. Comparison of horse chromosome 3 with donkey and human chromosomes by cross-species painting and heterologous FISH mapping. Mamm Genome 10(3),277-282.

Sambrook, J. and Russell, D. W., 2001, Molecular Cloning: A Laboratory Manual. 3d Ed. Cold Spring Harbor Press, N.Y.

Stephenson D., Lee K., Nagle D., Yen C., Morrow A., Miller D., Chapman V., and Bucan M., 1994. Mouse rump-white mutation associated with an inversion of chromosome 5. Mamm Genome 5(6), 342-348.

Trommershausen-Smith A., 1978. Linkage of tobiano coat spotting and albumin markers in a pony family. J Hered 69(4), 2 14-216.

What is claimed is:

1. A method for screening for a genotype for a Tobiano coat color pattern, comprising:

obtaining a biological sample containing a nucleic acid sample from an equine animal, said nucleic acid sample comprising equine chromosome ECA3q; and identifying a chromosomal inversion in a chromosome ECA3q, said inversion having a telomeric breakpoint located between a KIT gene and a KDR gene in a band ECA3q21 of said chromosome ECA3q and a centromeric breakpoint located between a ADH1D gene and a UNC5C gene in a band ECA3q13 of said chromosome ECA3q;

said step of identifying a chromosomal inversion comprising detecting at least one of a nucleic acid sequence surrounding the telomeric breakpoint of the inverted ECA3q chromosome and a nucleic acid sequence surrounding the centromeric breakpoint of the inverted ECA3q chromosome, or sequences complementary thereto;

wherein the presence of the chromosomal inversion as indicated by detection of at least one of said telomeric breakpoint or said centromeric breakpoint indicates that the equine animal possesses a genotype for a Tobiano coat color pattern.

2. The method of claim 1, wherein the centromeric breakpoint is between addresses chr3:41925230-41925231 of EquCab2 and the telomeric breakpoint is between addresses chr3:77663330-77663331 of EquCab2.

3. The method of claim 1, wherein the sequence surrounding the telomeric breakpoint of the inverted ECA3q chromosome is set forth in SEQ ID NO: 14 and the sequence surrounding the centromeric breakpoint of the inverted ECA3q chromosome is set forth in SEQ ID NO: 13.

4. The method of claim 1, wherein the step of detecting at least one of said telomeric breakpoint or said centromeric breakpoint comprises:

hybridizing a group of probes or primers consisting of the sequences set forth as SEQ ID NO: 8, SEQ ID NO: 9, and SEQ ID NO: 10 or sequences complementary to SEQ ID NO: 8, SEQ ID NO: 9, and SEQ ID NO: 10 to the nucleic acid;

amplifying the hybridized group of probes or primers; and detecting the presence or absence of a 209 bp amplification product indicative of the presence of the chromosomal inversion.

5. The method of claim 4, wherein the hybridized group of probes or primers are amplified by PCR.

6. The method of claim 1, wherein the biological sample is selected from the group consisting of a cell, a tissue, a hair follicle, a buccal swab, serum, plasma, whole blood, and a combination thereof.

7. The method of claim 4, wherein the presence of the 209 bp nucleic acid sequence is detected by any one of gel electrophoresis, DNA sequence analysis, or Southern blotting.

8. The method of claim 4, wherein the 209 by nucleic acid sequence is set forth in SEQ ID NO:11.

9. A method for screening for a genotype for a Tobiano coat color pattern by detecting a chromosomal inversion in an equine chromosome ECA3q, comprising:

obtaining a biological sample containing a nucleic acid from an equine animal;

hybridizing to said nucleic acid the group of probes or primers comprising the sequences set forth in SEQ ID NO: 8, SEQ ID NO: 9, and SEQ ID NO: 10, or sequences complementary to SEQ ID NO: 8, SEQ ID NO: 9, and SEQ ID NO: 10;

amplifying said hybridized group of probes or primers; and detecting the presence or absence of a 209 bp amplification product;

wherein detection of said 209 bp amplification product indicates the presence of an inversion in an ECA3q chromosome contained in said nucleic acid sample that is predictive of a Tobiano coat color genotype.

10. The method of claim 9, wherein the group of probes or primers are amplified by PCR.

11. The method of claim 9, wherein the presence of the 209 bp nucleic acid sequence is detected by any one of gel electrophoresis, DNA sequence analysis, or Southern blotting.

12. The method of claim 9, wherein the nucleic acid is obtained from a sample selected from the group consisting of a cell, a tissue, a hair follicle, a buccal swab, serum, plasma, whole blood, and a combination thereof.

13. The method of claim 9, wherein the 209 bp nucleic acid sequence is set forth as SEQ ID NO:11.

* * * * *

SEQUENCE LISTING

```
<160> NUMBER OF SEQ ID NOS: 15

<210> SEQ ID NO 1
<211> LENGTH: 21
<212> TYPE: DNA
<213> ORGANISM: Artificial Sequence
<220> FEATURE:
<223> OTHER INFORMATION: Trace file Accession # 1250295308

<400> SEQUENCE: 1
ctgcctccat cagagcctgc a                                             21

<210> SEQ ID NO 2
```

```
<211> LENGTH: 25
<212> TYPE: DNA
<213> ORGANISM: Artificial Sequence
<220> FEATURE:
<223> OTHER INFORMATION: Trace file Accession # 1378686387

<400> SEQUENCE: 2
tggaggtgac acagtgcact tcact                                          25

<210> SEQ ID NO 3
<211> LENGTH: 34
<212> TYPE: DNA
<213> ORGANISM: Artificial Sequence
<220> FEATURE:
<223> OTHER INFORMATION: Trace file intervening sequence primer

<400> SEQUENCE: 3
gatcagtgta gacgtagtgt gacagagacc cagg                                34

<210> SEQ ID NO 4
<211> LENGTH: 36
<212> TYPE: DNA
<213> ORGANISM: Artificial Sequence
<220> FEATURE:
<223> OTHER INFORMATION: Trace file intervening sequence primer

<400> SEQUENCE: 4
ggcaaacaga gggccaaatg atagatcagt gtagac                              36

<210> SEQ ID NO 5
<211> LENGTH: 35
<212> TYPE: DNA
<213> ORGANISM: Artificial Sequence
<220> FEATURE:
<223> OTHER INFORMATION: Trace file intervening sequence primer

<400> SEQUENCE: 5
tgtgctctag caagggtgga gcatgtttca ttaag                               35

<210> SEQ ID NO 6
<211> LENGTH: 2593
<212> TYPE: DNA
<213> ORGANISM: Equus caballus

<400> SEQUENCE: 6
ctttgctctt gtgttacagg ttcactcaga gaacgcaagc tttggtgcac cttttcatta     60
cactgcctgt aaggcttcca ggaatgagtg cgggcgattt gctgtgtttt gacatttttt    120 tccccttttct gagagctgtc agttgagagg cagtatcctc ttgtgagaga gtttggtgcc   180
ggctgcaaaa ttaaaggcaa gaataaccca caaataagag agcatgagtg ccagatatc    240 tctcaatcct gatatgggct gtggaaggcc atgtgtgttt atgtcctccc tccagctgga    300
gccaagaaga ggcatccgga gtgatggcat ccagaggctg caggaggcag ggcctgtggg    360
ggtataaagg cagtgggatg acaggggcg ttctgctgga aggtgtacga ggcccttgtt    420
gaagccagtg aagtgcactg tgtcacctcc agtttttcttg gggctggact gggctatcca   480
ttgaagaaat ggggtggaga acccaggctt agtcattttt ttcctcccca gtttccgctg    540
gttgtgggct ggaatgtgac atgttgtttt ctttactaat tggtcataa ttttaaaag     600 ctgatgatct ccttttcctta aagtaccagg tctccatatc aaaccagggg aaactgtgcc   660
gtggggttgc tggtgagtct tgctccctag aagcccgtta ggtgatcgt gtcgtcagaa    720 gacagaagga ggaatggggg ttccctccct actgctctgg agaactgtgc tctagcaagg    780
```

-continued

```
gtggagcatg tttcattaag tttcctgggg gcaaacagag ggccaaatga tagatcagtg    840
tagacgtagt gtgacagaga cccaggcaga gctctgcctc ccggcctgca gcagggctc     900 ccgacttcct tgagtatgtg aatttcctct tcaaactcca gaatcattca gaacctatgc    960
tagagtggga gtagctgttg actgagaaaa cgaaagatga ttcaaaaaat tattaaatat   1020
gcttaaaacc atatttgagt acaacgagag gcactcacaa ctagaaaaca caactatgta   1080 ctgggggct tgggagaa aaagaagaaa aaagaagat tggtaatagt tgttagctta       1140
ggtaccaatc ttttaaaaaa aaaagcatat tactcgataa tcaagttata taatggcata   1200
cagttaaaac caaagttgta aagggaccat cacaatcgtt tctgcaattg gacaaatact   1260
caacacacac cccttgtgtc gattcatccc actcttggca gtgcatcctg tcgatgtgta   1320
caatggcagc catgatgcgt tcctccattt cctcaggact atgagactct tggtgtatgc   1380
ccacgagatg tcaatggtgt gatgacctga gctcccgggt ggctgctgct ccagagttaa   1440
gtcaatgttt aaatagaaag ccctacccag tgccctggga tagattcatg aaagaacttc   1500
tggactgctg gaaaatgagg tttcaaagac ttcctgaagc tgtggggaaa ccccttcagt   1560
gtatcctgac actatgttct tcacacacac acacacagag ttggcatctg tattgatgta   1620
tcacaaaagt catgggggat cccttacacg ttcaatcacc acgtgttggt atttggtgcc   1680
ccgtatatgg atgctgtgaa gaatcacatt tttagtgaaa tgaacacaga cttatcattg   1740
aatttgagac aacctgcaaa ggcaacttcg tcttctgtct gagtctgaaa gcagcagctg   1800
aagttttatc gttttacccc atctgcctcc atcagagcct gcagagggtg caagaaggtt   1860
tcatcttcca tcgcttatgg agaaggtgcc agaccatggt ctgaggaaca caatactctc   1920
agccagccct ctttatggac tccttggggc tctgctgaat gagacaaaaa tgattccgtt   1980
ttcttaagac atgtgaaatg taagcacaca caagttggtg cctactacat gttgctagtc   2040
attgagtagt acattttttt cttcaaagcg ttcaattttt tgaatcatca tgtacatact   2100
ggccaaaaac tacaagtaac gcttttgagt taatttgcat ttttctcatc accaaagcat   2160
ctaaacacac cataaaatag ttagacacat atacatcata ccacagtaat gtggcccttt   2220
ataaagtggc atacttttta tagctacctc cgctgatcct cagaaaaatc ctgtacgata   2280
tgcaccatga tccccatttt gcagataagg aaactgggac tcagagagac agccactgat   2340
caaggtcttg cacacagcag attgtggaac taggattccc ttcaggcctg gaaacccaca   2400
gccgctccta caccatgtgg ccttctcaaa taaggaaaaa cctctgattt cttaaaatag   2460
tattgtgcta ttattctctt ttcttggtat ataaaagtaa aggtttaaat ctggcatttt   2520
gtttgttgta ttaggttgaa gtgtgcgaaa ctgctgatac ttaccatttc tgacctacgt   2580
caacctatag ttt                                                      2593
```

```
<210> SEQ ID NO 7
<211> LENGTH: 1520
<212> TYPE: DNA
<213> ORGANISM: Equus caballus

<400> SEQUENCE: 7
ctttgctctt gtgttacagg ttcactcaga gaacgcaagc tttggtgcac cttttcatta    60
cactgcctgt aaggcttcca ggaatgagtg cgggcgattt gctgtgtttt gacatttttt   120
tcccctttct gagagctgtc agttgagagg cagtatcctc ttgtgagaga gtttggtgcc   180
ggctgcaaaa ttaaaggcaa gaaataacca caaataagag agcatgagtg gccagatatc   240
tctcaatcct gatatgggct gtggaaggcc atgtgtgttt atgtcctccc tccagctgga   300
```

```
gccaagaaga ggcatccgga gtgatggcat ccagaggctg caggaggcag ggcctgtggg    360
ggtataaagg cagtgggatg acaggggggcg ttctgctgga aggtgtacga ggcccttgtt    420
gaagccagtg aagtgcactg tgtcacctcc agttttcttg gggctggact gggctatcca    480
ttgaagaaat ggggtggaga acccaggctt agtcattttt ttcctcccca gtttccgctg    540
gttgtgggct ggaatgtgac atgttgtttt ctttactaat tgggtcataa ttttaaaaag    600
ctgatgatct cctttcctta aagtaccagg tctccatatc aaaccagggg aaactgtgcc    660
gtggggttgc tggtgagtct tgctccctag aagccctgta ggtgatctgt gtcgtcagaa    720
gacagaagga ggaatggggg ttccctccct actgctctgg agaactgtgc tctagcaagg    780
gtggagcatg tttcattaag tttcctgggg gcaaacagag ggccaaatga tagatcagtg    840
tagacgtagt gtgacagaga cccaggcaga gctctgtgta ctttctgtta tactgctctg    900
aataaatatc tgaaatgcct tgagtgctga atgccaaaga tgattgaaat ccctctgagc    960
cgtaaattta aaatgtgttc tatgtgctga agattttgca ttatgtgaaa gacataattg   1020
gatactctgt ggtgaaagac aggataaatg ttacagaatt ctctgtacct aattcctctc   1080
cttttaaaag taaaaataaa ttgtatcagc ttacatgaaa gtagaaaata aaatatataaaa  1140 tgatacaaat ccacatctat ttttttctct ctgattcaag tagcccctaa tttaaacaca   1200
cagactagca gctgaatttt tgttgttatt gttaaagtca gtctagcact tcattgaatg   1260
aagaagaatc cgtctgttta gtgaggaatt aggtcctctg aaacttcaga cagtctgcca   1320
aacctcagag attctgacct tctgctacca ctgccaaatc ataccagagt catttgtcag   1380
cagaattttc caaacagggt tagccagata gatgagcaga cattacacgg ctgctttaaa   1440
acctctaatt tcagtggcac tgaataggct gacaatttcc caagccgact agagagaaac   1500
aaggcgttaa aaggatttat                                              1520

<210> SEQ ID NO 8
<211> LENGTH: 34
<212> TYPE: DNA
<213> ORGANISM: Artificial Sequence
<220> FEATURE:
<223> OTHER INFORMATION: Common forward primer

<400> SEQUENCE: 8
tgatagatca gtgtagacgt agtgtgacag agac                                34

<210> SEQ ID NO 9
<211> LENGTH: 29
<212> TYPE: DNA
<213> ORGANISM: Artificial Sequence
<220> FEATURE:
<223> OTHER INFORMATION: non-tobiano primer

<400> SEQUENCE: 9
aacagctact cccactctag cataggttc                                      29

<210> SEQ ID NO 10
<211> LENGTH: 39
<212> TYPE: DNA
<213> ORGANISM: Artificial Sequence
<220> FEATURE:
<223> OTHER INFORMATION: tobiano reverse primer

<400> SEQUENCE: 10
ttcaccacag agtatccaat tatgtctttc acataatgc                           39

<210> SEQ ID NO 11
```

```
<211> LENGTH: 209
<212> TYPE: DNA
<213> ORGANISM: Artificial Sequence
<220> FEATURE:
<223> OTHER INFORMATION: 209 bp tobiano unique PCR product

<400> SEQUENCE: 11
tgatagatca gtgtagacgt agtgtgacag agacccaggc agagctctgt gtactttctg      60
ttatactgct ctgaataaat atctgaaatg ccttgagtgc tgaatgccaa agatgattga     120
aatccctctg agccgtaaat ttaaaatgtg ttctatgtgc tgaagatttt gcattatgtg     180
aaagacataa ttggatactc tgtggtgaa                                       209

<210> SEQ ID NO 12
<211> LENGTH: 152
<212> TYPE: DNA
<213> ORGANISM: Artificial Sequence
<220> FEATURE:
<223> OTHER INFORMATION: Non-tobiano 152 bp PCR product

<400> SEQUENCE: 12
tgatagatca gtgtagacgt agtgtgacag agacccaggc agagctctgc ctcccggcct      60
gcagcagggg ctcccgactt ccttgagtat gtgaatttcc tcttcaaact ccagaatcat     120
tcagaaccta tgctagagtg ggagtagctg tt                                   152

<210> SEQ ID NO 13
<211> LENGTH: 5001
<212> TYPE: DNA
<213> ORGANISM: Equus caballus

<400> SEQUENCE: 13
tatatttaaa tactcagagc aattatgaaa ccccacacag cctcaacaga ccatttaacc      60
ttgagcagtg taatttccgg gtgtgtcctg aaaataagtt ggcaactaat catatataga     120
agtaaataaa tgagtcaaaa tatgtctaaa atgaagttat aagtcaagta agtattgttt     180
tgtatctaaa ggaataatgg gtttgttttt agtggaattg atcacttctt ttttggcagt     240
aattaagtag tagaccaact tggaatttta gaatcataaa agtgaaattc attttttaata    300 aattttttta aataaaattc ttagaaaatg gaattcaatc tacgctgtgg gattttgttt     360
ctttggcgtg gcaatggagc tgacattgca gaatgagatg tggcgaagaa tggctgctct     420
ccaacactgt atacaggttt tcttaaatta acggctagat tgtaaacttc accaaagcag     480
agaacacctt cttttttgact gttttatccc tggccctcag cagagcgctg gcatatagga     540
gatcatagct gaaatagctg ctgttttttac cttgaacact gttctctggt acaacaaaaa    600
tgataaaagt catcaagaga ggttagagtt tttacgtaaa tgttatgcat ttaaaagtat     660
aagatatatg tttgtattaa aatagtatct acttttaatc agtgacatgt gattccttct     720
ttaattgaaa agaaagctgt cacattttaa tcaatggtct atgacagtgt aggaggcgtg     780
atagccaata aaacattttt acatggcact tttcctcact cctttgaaat cggaagcctc     840
taaatagata ttctgaacaa aatatatagc ccaagtacga tccaacttag aaatggaaaa     900
aatacagaaa agtttattgt aacatattgg aaatcttaat atgatgaaac aaaatgagct     960
gcccaaattt tggggacgat ggttctgcat ttgcaggtca ttttggtaat taaaatatgg    1020
taaataccag ctgttttctta tgctcttaga ttatctgttc atgttaccag gatgattttg    1080
tgaagccgag tatcagactc catgtcttag caggctcaaa ggtcaaaatt agaatcttaa    1140
attgaagttc gcattaatcc agattgccat ttgcttactt tttgatagca gtccacctaa    1200
```

```
actgaaatga gtaatagaga ttttcatgtc tgaatgatat tcctgccagc accaccaact    1260
gttgaatgtt aagtatgaga tttggcaggt gcagagattt ttagtcacct tcaaaaagca    1320
atatgcagac acccaagcca aacagcttat atattaacaa atcaacatc caaaccatct     1380 gccaatggaa caaacatgtc agtcatcttt ccatttgatt ggcagggttt ctagaaatga    1440
atgattttaa acattatttc tcatcccaaa aaacacaca gggaatttta tttacctggt     1500
aattgagctg actctgggca aaattatgta gttaaaaacg tcttcatctt ctccttgctc    1560
tttcattgcc tgctcctccg ttaccactgt gtaccctgca cacccatcct agcacctgtt    1620
attaacttat tgactcctgc ctgctgctgt gccaaacagc gccaggatga gttaatgctt    1680
gcatctgatt tatttcctct tagccaacat acgttttta ggactctgct tataggcgat      1740
tatatttagt aattaaatca ggtaaaccaa ttctttaaa ttaaattctt aagttaaaaa      1800
tgactgacat ataaaacatg atttttcacc ctctaaaagt ctttaaagcg taagcataaa    1860 tctttaaac gcttgtttct ctctagtcgg cttgggaaat tgtcagccta ttcagtgcca      1920
ctgaaattag aggttttaag cagccgtgta atgtctgctc atctatctgg ctaaccctgt    1980
ttggaaaatt ctgctgacaa atgactctgg tatgatttgg cagtggtagc agaaggtcag    2040
aatctctgag gtttggcaga ctgtctgaag tttcagagga cctaattcct cactaaacag    2100
acggattctt cttcattcaa tgaagtgcta gactgacttt aacaataaca acaaaaattc    2160
agctgctagt ctgtgtgttt aaattagggg ctacttgaat cagagagaaa aaaatagatg    2220
tggatttgta tcattttata ttttattttc tactttcatg taagctgata caattttattt    2280 ttacttttaa aaggagagga attaggtaca gagaattctg taacatttat cctgtctttc    2340
accacagagt atccaattat gtcttcaca taatgcaaaa tcttcagcac atagaacaca     2400
ttttaaattt acggctcaga gggatttcaa tcatctttgg cattcagcac tcaaggcatt    2460
tcagatattt attcagagca gtataacaga aagtacacag cagattgtaa tttaaatgct    2520 gtacttttg caacatatat ttgcaataaa agcatagaga atatgtaaaa ataagaatgt     2580
attatgagta ctgcacattt tcactacacc ctttgataag ggaattcttg catactttca    2640
tgtaatagac atttctcag tacaactttg tatggaatgc ataggacaca cacctgatgc      2700
tctgttcttc cagccatgtg ggttgtttgt gtccacatta gggcacttac acctccatgt    2760
ggagaccatt tctctatgca gtagagagca aatagaaata ttttaatatt ggatttattt    2820
tttggtatac aaccagacaa tagtgcagaa gatagactgg agggttaggt gccaagaagt    2880
caaattaagg agtcgttgca ataatccatg aggcctgaag aaggcttcaa ttaagaaaag    2940
agagagagcc agagagaatg gagtagggat ttaacatttt ctaggaagat aaggaaaaga    3000
atggcaatcc aggagaaaga atgagacacg gttgccaata aacgtgatta agaaaaggca    3060
tgcagcacga aatgagcaga acttttgcaa aacctatatt taaggaatta gcaacaataa    3120
caaaaaagta gtggctatct tgagaagtta tctcaaggac aattaaccaa gagttgatga    3180
gtttcaggat gttgagaatg aatacagctt tggtcagcgc aaatgctgaa agtaagctga    3240
catttctacc aaaggtcaca gggaagtaga agccctgtgg tctccgtgtg cacagaaaac    3300
tgagagctta tttgaaacaa ataagagcaa gagaaaaaaa gagccttaaa gaaaaggatt    3360
tgatggttga caacaggcat atcagagagt ttgcaaatag cccatttgga tttgaaaatt    3420
tggacctctt gcgatgtctg tgagtgtgat tttattagaa tggtggagat ggaagtcaaa    3480
ttttaatcga tttaggtgat gcggattggg gaaattgggg aaacaagtgt gggcaatttc    3540
tgttaaataa tttggtgact aagagaagga gggagacagg tttcaatttg aagggtataa    3600
```

```
gagttcagaa aagtacattt gttcattttt aaaaataaat atggaaggag ggaacctgag    3660
tatatttctg tggtgaaagg ttagagagaa gtggaaatag aatatctaga aaagaccaga    3720
gcaaattggt ggtgtaattt aagaggggca aagtgtgcag gtgaaagtgt gaaccttagg    3780
agtcggaagc atggacgcta ggaggtatag acaagaactg gagcaggagg tggctaggca    3840
ctctccccat tggtggcttc tattgcattt atgaagggat cagagatatg ctgatggtga    3900
gacaagtaga aatcttgtag ggaactagag gagagagaat accagaattg gactactgga    3960
cactttgaat gcagtaagca cctgcttaag ataaatactc ccctcactaa ggaatctctg    4020
agaatggtgg cttttacaa tattgcacct ggtgcttatc acctcactct ttatgagttt    4080
cacaaatatt tagtgagctc agcccatgtg cctagaacta tatcaaggcc tagtaggttt    4140
tataggacaa ggagaagaga tggctcttca aggagcttgg gcttctgttc tgtcgggtag    4200
tattgggcca aggagtagtt tctttcagcc cattttcttc ttctattgaa cagtatttca    4260
ttgtcatatt attccatttg ctgttcatat gtgactgctt cttggttgca ttgtactttc    4320
ctgggcgtgt tatctatatt ttgtgaatgg agaaaggatc cataatgaca gcattttgtt    4380 cttttctccct atgctttcaa atagtgtcag gatgcttatt tatcagtgct gcctgctgtg    4440
agcagctctg tgccaattta gcatcatcag gaacaactac attaaggtga tggtccctgt    4500
gcaagatccg tgagctcgtt ccactaattc atgaaaacat attcatttat ttttagctaa    4560
taaaacgatc ttcaaactgc ttgttcaggc atacatcacc aaaacatttc ctatgtcttt    4620
aatgttttca accttcatta tcttttcact ccactaattt agaatgtgga gggaaatctc    4680 tcaaattttta tgaaattata ctgccatcat ttaaccttttg ctattatgct gatttattta    4740
tttattcatt tatttctta tggcatagga atacataata aataatgaga atagagttag    4800 caactttaa aaatagaaag tacttactag aataaaaata gttacctgac agaaagtttt    4860
aaaaataatc atttcttcta tttattcact ccacatatgc taaaaatttt agtggaaact    4920
actggtcccg cttccttccc tgcaaagcat ccatttccct cctttgtcac tgggaaggag    4980
tcctagttcc agtgggttga t                                             5001
```

<210> SEQ ID NO 14
<211> LENGTH: 5001
<212> TYPE: DNA
<213> ORGANISM: Equus caballus

<400> SEQUENCE: 14

```
ctcacctatg agaccgcttg gagaagttgg aagggcccaa gggtatatcc aaaaataact     60
gacaagcccc tcagccttca cccaggagtt ccaggattgt cgttccctga ggcaaagctg    120
gcaaggtttt ggtggcggca gctaggagaa agcacctctg gaacatccct cctcggtttg    180
aaattctgta agatgagcag tgtctcagca ggaaggctga gttcgccagc tgataggcag    240
gcagctgaca ggccgcagag ccggggtgca gaggatgact ctgctcggga agtctgctgg    300
agctgcagct tgcccaggct ctctgctctg acactcagca tttgcctcct cttgaaactg    360
atctcacctt gttttccacc tcccctcatc cacacagaag gtaggatttt ttttttttt    420 gaggaagatt agccctgagc taacatctgc tgccaatcct cctctttttg ctgaggaaga    480
ctggccctga gctaacattc atgccatct tcctctatgt tatatatggg acacctgcca    540
cagcatggct tgccaagcag tgctatgtcc gtacccagga tccgaaccgg caaaccctgg    600
gctgccaaag gggaacgtgc acactgaacc gatgcacctc tgggctggcc ccataagtt    660 aggattttttg attttcaaaa tttttaaaat aaaattatct gttggggctg gccccgtggc    720
```

```
caagtggtta agttcgcgcg ctccgctgca ggcgacccag tgtttcgttg gttcgagtcc    780
tgggtgcgga catggcactg ctcatcagac cacgctgagg cagcgtccca catgccacaa    840
ctagaagaac ccataacgaa gaatacacaa ctatgtaccg gggggctttg gggagaaaaa    900
ggaaaaaata aaatctttaa aaaaaaaaat aaaaaataaa aaaataaaat aaaattatct    960
gttcatgttt ttaacagcca tagaaattat taactcctaa ttatagaaac agtggaaaac   1020 aaaccgtac aaagaataaa ggtgcccaga gacccatagt caccagacaa aggcaaccac    1080
gtttatattt tggcctattt gctatcagtc attaatgtgt gtgtctaggc gcccacatgt   1140
gtgaatgcac atattccaac tttaacacga caaaataaaa caaagtttgc acccaagtta   1200
aagccatggt gggtgacact caacgactca catttgcagt taagaccaag gactaccagt   1260
ggccttgcct gggccacgtg acactgccga gggggccgtt acagttctaa tttacagttt   1320
ggctaagcca ggcggcttgg tgataagcac agcttgttta tttgtctttg atggatgcca   1380
ggtggattgt ggtcagacaa tcttccttca gcagcctcag cactttgcat ccacggagct   1440
agcgtgaggc cctcccctga ggaaaacgca ggtcacacaa tgagcgccca caacaaaggg   1500
acggtcacag tggtggcggc accaaacgag gacaaagaag cgcttgggcg gagaggaaag   1560
aggaagaaag cagggagggc ccaggagacg ccaccaggca ggcaggtggc caggcaagct   1620
gaccagcttt gctcttgtgt tacaggttca ctcagagaac gcaagctttg gtgcacccttt  1680 tcattacact gcctgtaagg cttccaggaa tgagtgcggg cgatttgctg tgttttgaca   1740
tttttttccc ctttctgaga gctgtcagtt gagaggcagt atcctcttgt gagagagttt   1800
ggtgccggct gcaaaattaa aggcaagaaa taaccacaaa taagagagca tgagtggcca   1860
gatatctctc aatcctgata tgggctgtgg aaggccatgt gtgtttatgt cctccctcca   1920
gctggagcca agaagaggca tccggagtga tggcatccag aggctgcagg aggcagggcc   1980 tgtggggta taaaggcagt gggatgacag ggggcgttct gctggaaggt gtacgaggcc    2040
cttgttgaag ccagtgaagt gcactgtgtc acctccagtt ttcttggggc tggactgggc   2100
tatccattga agaaatgggg tggagaaccc aggcttagtc atttttttcc tccccagttt   2160
ccgctggttg tgggctggaa tgtgacatgt tgttttcttt actaattggg tcataatttt   2220
aaaaagctga tgatctcctt tccttaaagt accaggtctc catatcaaac caggggaaac   2280
tgtgccgtgg ggttgctggt gagtcttgct ccctagaagc cctgtaggtg atctgtgtcg   2340
tcagaagaca gaaggaggaa tgggggttcc ctccctactg ctctggagaa ctgtgctcta   2400
gcaagggtgg agcatgtttc attaagtttc ctggggcaa acagagggcc aaatgataga    2460
tcagtgtaga cgtagtgtga cagagaccca ggcagagctc tgcctcccgg cctgcagcag   2520
gggctcccga cttccttgag tatgtgaatt tcctcttcaa actccagaat cattcagaac   2580
ctatgctaga gtgggagtag ctgttgactg agaaaacgaa agatgattca aaaaattatt   2640
aaatatgctt aaaaccatat ttgagtacaa cgagaggcac tcacaactag aaaacacaac   2700
tatgtactgg ggggctttgg ggagaaaaag aagaaaaaaa gaagattggt aatagttgtt   2760
agcttaggta ccaatctttt aaaaaaaaag catattactc gataatcaag ttatataatg   2820
gcatacagtt aaaaccaaag ttgtaaaggg accatcacaa tcgtttctgc aattggacaa   2880
atactcaaca cacacccctt gtgtcgattc atcccactct tggcagtgca tcctgtcgat   2940
gtgtacaatg gcagccatga tgcgttcctc catttcctca ggactatgag actcttggtg   3000
tatgcccacg agatgtcaat ggtgtgatga cctgagctcc cggtggctg ctgctccaga    3060 gttaagtcaa tgtttaaata gaaagcccta cccagtgccc tgggatagat tcatgaaaga   3120
```

```
acttctggac tgctggaaaa tgaggtttca aagacttcct gaagctgtgg gaaaacccctt    3180 cagtgtatcc tgacactatg ttcttcacac acacacacac agagttggca tctgtattga    3240
tgtatcacaa aagtcatggg ggatccctta cacgttcaat caccacgtgt tggtatttgg    3300
tgccccgtat atggatgctg tgaagaatca cattttttagt gaaatgaaca cagacttatc    3360
attgaatttg agacaacctg caaaggcaac ttcgtcttct gtctgagtct gaaagcagca    3420
gctgaagttt tatcgtttta ccccatctgc ctccatcaga gcctgcagag ggtgcaagaa    3480
ggtttcatct tccatcgctt atggagaagg tgccagacca tggtctgagg aacacaatac    3540
tctcagccag ccctctttat ggactccttg gggctctgct gaatgagaca aaatgattc     3600 cgttttctta agacatgtga aatgtaagca cacacaagtt ggtgcctact acatgttgct    3660
agtcattgag tagtacattt ttttcttcaa agcgttcaat ttttttgaatc atcatgtaca   3720 tactggccaa aaactacaag taacgctttt gagttaattt gcatttttct catcaccaaa    3780
gcatctaaac acaccataaa atagttagac acatatacat cataccacag taatgtggcc    3840
ctttataaag tggcatactt tttatagcta cctccgctga tcctcagaaa atcctgtac     3900 gatatgcacc atgatcccca ttttgcagat aaggaaactg ggactcagag agacagccac    3960
tgatcaaggt cttgcacaca gcagattgtg gaactaggat tcccttcagg cctggaaacc    4020
cacagccgct cctacaccat gtggccttct caaataagga aaaacctctg atttcttaaa    4080
atagtattgt gctattattc tcttttcttg gtatataaaa gtaaaggttt taaatctgga    4140
attttgtttg ttgtattagg ttgaagtgtg cgaaactgct gatactttac catttctgac    4200
cctacggttc aacctaatag ttttcttctc tgggggaaag aaagaaggaa ggaaggaaag    4260
aaggagaaaa tgcaatgcat gaaaacagag agcaataaaa agatcaaaaa gcacagaagg    4320
aggaagaaaa tgagggaagg aagaaggtat aagaagaaat tagaaattac tagtaaagct    4380
ttgtcactct ttctaaactc tcctgcccctt cagtttcttc ccccacagtc ttggcttta    4440 ctgtctattg cctttgatca ggattttctc agtcaccaga ctccttaagt aatcaacaga    4500
gaccaactgt atcatattgt ctttcattct ttatttattt taaacaagga ttgcgcagat    4560
ttctagccac cacccccgagg gggtaagagg gaagaaaaga tcgacagaac aaagtcttgc    4620
atttattagg accgtctaaa tacgactttc tcttctcggg ggaaaaacac tggaccaaaa    4680
cgaaatgccc tcaatgtaca aatttgtaga aatgtaaagt tagcatacat tgaagtttca    4740
gatgagaaac ttgaccttaa tgttgaaaga agagagatga gaagacaaaa aaaatgaaag    4800 aaacctttt aaataaataa ttagcttgga gatgatataa agtgtttttct aaatcaatcc    4860 attcatagga agaaataaac acatttgaac aatttgatta acacatgtga ataacaaatg    4920
ataaagctag ggagcagctg aagtcctgcc actgaagact ttaagggata aatgctctca    4980
ccccctaatg ctgcctctgg a                                              5001
```

<210> SEQ ID NO 15
<211> LENGTH: 24
<212> TYPE: DNA
<213> ORGANISM: Artificial Sequence
<220> FEATURE:
<223> OTHER INFORMATION: Centromeric primer

<400> SEQUENCE: 15
atgtgcagta ctcataatac attc                                           24